(12) United States Patent
Frederix et al.

(10) Patent No.: US 8,043,868 B2
(45) Date of Patent: Oct. 25, 2011

(54) METHOD AND APPARATUS FOR DETECTING AN ANALYTE

(75) Inventors: Filip Frederix, Leuven (BE); Kristien Bonroy, Averbode (BE)

(73) Assignee: IMEC, Leuven (BE)

( * ) Notice: Subject to any disclaimer, the term of this patent is extended or adjusted under 35 U.S.C. 154(b) by 194 days.

(21) Appl. No.: 11/555,544

(22) Filed: Nov. 1, 2006

(65) Prior Publication Data

US 2007/0117151 A1 May 24, 2007

Related U.S. Application Data

(63) Continuation-in-part of application No. 10/322,901, filed on Dec. 18, 2002, now abandoned, which is a continuation-in-part of application No. 11/175,729, filed on Jul. 5, 2005.

(60) Provisional application No. 60/345,169, filed on Dec. 21, 2001, provisional application No. 60/584,953, filed on Jul. 2, 2004, provisional application No. 60/733,277, filed on Nov. 2, 2005.

(51) Int. Cl.
*G01N 33/543* (2006.01)

(52) U.S. Cl. .......... 436/518; 435/7.1; 436/164; 436/172

(58) Field of Classification Search .............. 435/6, 7.1, 435/7.92–7.94, 808; 436/164, 172, 518, 436/523–525; 422/82.05, 82.07
See application file for complete search history.

(56) References Cited

U.S. PATENT DOCUMENTS

| | | | |
|---|---|---|---|
| 4,802,761 A * | 2/1989 | Bowen et al. .................. 356/301 |
| 5,611,998 A | 3/1997 | Aussenegg et al. |
| 5,866,433 A * | 2/1999 | Schalkhammer et al. ..... 436/525 |
| 6,127,129 A * | 10/2000 | Corn et al. .................. 435/6 |
| 6,268,125 B1 | 7/2001 | Perkins |
| 6,582,921 B2 * | 6/2003 | Mirkin et al. .................. 435/6 |
| 6,685,986 B2 * | 2/2004 | Oldenburg et al. ........... 427/214 |
| 6,770,441 B2 * | 8/2004 | Dickinson et al. ................ 435/6 |
| 7,129,096 B2 | 10/2006 | Chilkoti et al. |
| 2002/0095073 A1 | 7/2002 | Jacobs et al. |
| 2002/0128234 A1 | 9/2002 | Hubbell et al. |
| 2002/0160522 A1 * | 10/2002 | Rubinstein et al. ........... 436/164 |
| 2003/0170687 A1 * | 9/2003 | Chilkoti et al. ................... 435/6 |
| 2004/0023293 A1 * | 2/2004 | Kreimer et al. ................. 435/7.1 |
| 2005/0100947 A1 * | 5/2005 | Wagner ............................ 435/6 |
| 2006/0228366 A1 * | 10/2006 | Watkins ..................... 424/155.1 |
| 2008/0131869 A1 | 6/2008 | Frederix et al. |

FOREIGN PATENT DOCUMENTS

| | | |
|---|---|---|
| EP | 0469377 A2 | 2/1992 |
| WO | WO 99/21934 * | 5/1999 |
| WO | 01/44813 A2 | 6/2001 |

OTHER PUBLICATIONS

Saerens, Dirk et al., "Engineering Camel Single-Domain Antibodies and Immobilization Chemistry for Human Prostate-Specific Antigen Sensing", Analytical Chemistry, vol. 77, No. 23, Dec. 1, 2005, pp. 7547-7555.

Frederix, F. et al., "Enhanced Performance of an Affinity Biosensor Interface Based on Mixed Self-Assembled Monolayers of Thiols on Gold", Langmuir, vol. 19, No. 10, 2003, 7 pages.

Geukens, Nick et al., "Analysis of Type I Signal Peptidase Affinity and Specificity for Preprotein Substrates", Biochemical and Biophysical Research Communications, vol. 314, 2004, pp. 459-467.

Huang, Lieven et al., "Prostate-Specific Antigen Immunosensing Based on Mixed Self-Assembled Monolayers, Camel Antibodies and Colloidal Gold Enhanced Sandwich Assays", Biosensors and Bioelectronics, vol. 21, 2005, pp. 483-490.

Jin, Yongdong et al., "Controlled Nucleation and Growth of Surface-Confined Gold Nanoparticles on a (3-aminopropyl) trimethoxysilane-Modified Glass Slide: A Strategy for SPR Substrates", Analytical Chemistry, vol. 73, No. 13, Jul. 1, 2001, pp. 2843-2849.

Nath, Nidhi et al., "Label-Free Biosensing by Surface Plasmon Resonance of Nanoparticles on Glass: Optimization of Nanoparticle Size", Analytical Chemistry, 2004, 9 pages.

Okamoto, Takayuki et al., "Local Plasmon Sensor with Gold Colloid Monolayers Deposited Upon Glass Substrates", Optics Letters, vol. 25, No. 6, Mar. 15, 2000, pp. 372-374.

Zeman, Ellen J. et al., "An Accurate Electromagnetic Theory Study of Surface Enhancement Factors for Ag, Au, Cu, Li, Na, Al, Ga, In, Zn and Cd", J. Phys. Chem., vol. 91, 1987, pp. 634-643.

Cliquet, P. et al., "Generation of Class-Selective Monoclonal Antibodies Against the Penicillin Group", J. Agric. Food Chem., vol. 49, 2001, pp. 3349-3355.

Frens, G. et al., "Controlled Nucleation for the Regulation of the Particle Size in Monodisperse Gold Suspensions", Nature Physical Science, vol. 241, Jan. 1, 1973, pp. 20-22.

\* cited by examiner

*Primary Examiner* — Melanie J Yu
*Assistant Examiner* — Gary W Counts
(74) *Attorney, Agent, or Firm* — McDonnell Boehnen Hulbert & Berghoff LLP

(57) ABSTRACT

A method for determining a concentration of an analyte is provided. The method includes providing a substrate including a conductive region and a recognition layer where the conductive region has a first surface operatively coupled with the recognition layer; The method also includes contacting the substrate with the sample to bind at least some of the analyte that may present in the sample with the recognition layer; The method further includes directing radiation through the conductive region and the recognition layer, where the conductive region comprises at least one particle and a combination of the at least one particle effect when the radiation is directed through the conductive region and the recognition layer; The method still further includes measuring at least a part of a spectrum of the radiation that is absorbed or transmitted by or through the substrate, the at least part of the spectrum being related to one or more of the at least one particle effects; The method further includes determining a change of the at least part of the spectrum as compared with a reference spectrum and determining the concentration of the analyte from the change.

24 Claims, 30 Drawing Sheets

Figure 14: Schematic drawing of an antibody-antigen interaction on a nanoparticle film, covered with self-assembled monolayers of thiols, which bind antibodies, which can bind antigen.

*Figure 15: Enzymatic cutting of an antibody to F(ab')₂ using pepsin*

*Figure 16: Chemical reduction of a F(ab')₂ fragment to two fully active Fab' fragments.*

Figure 17 Top: Conventional antibody structure and its fragments (Fab, Fv, ScFv)
Bottom: Heavy Chain antibody and its VHH fragment Figure 18: Schematic representation of the performed experiment concerning PSA detection using VHH fragments Figure 19: The detection of different concentrations of PSA measured after different time frames using the differential transmission plasmon biosensing measurements The blue bars indicate the results using camel antibody fragments as bioreceptors, while the purple bars indicate some results realized using normal mouse monoclonal antibodies.

*Figure 20: A schematic illustration of a TPB sandwich approach. From bottom to top: quartz substrate, mercaptosilane adhesion layer, Au 50 nm gold nanoparticles, mixed self-assembled monolayer, camel antibody fragment (VHH), PSA, secondary anti-PSA antibody functionalized with 20 nm gold nanoparticles.*

*Figure 21. The detection of 10 ng/mL of PSA via a direct measurement or via an sandwich approach using gold labeled secondary antibodies.*

*Figure 22: (a) penicillin specific antibodies are bound to the surface modified with the analyte analogue (ampicillin) (b) the surface bound antibodies are replaced by the ampicillin molecules in the sample.*

*Figure 23: Binding of the anti-penicillin antibodies to the ampicillin modified nanoparticle film in function of the time and the decrease of the signal to its starting value after subjecting the surface to a high concentration of ampicillin*

Figure 24: Changes of the maximum absorption during binding of the anti-penicillin antibodies to the ampicillin modified nanoparticle film in function of the time and this in the presence of different concentrations of ampicillin (100 ng/ml – 100 µg/ml).

Figure 25: Schematic presentation of the different immunoassay formats that can be used a) the direct assay, b) the sandwich assay, c) the indirect competition assay and d) the indirect inhibition assay Figure 26: Mixed self-assembled monolayer to functionalize the surface of the gold nanoparticles.

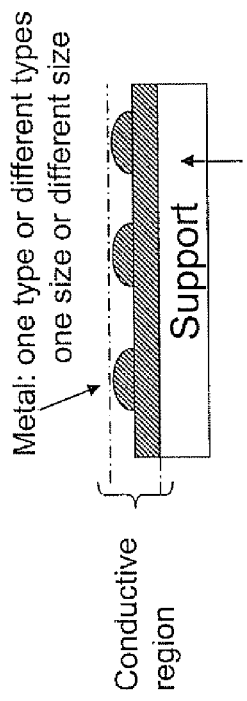
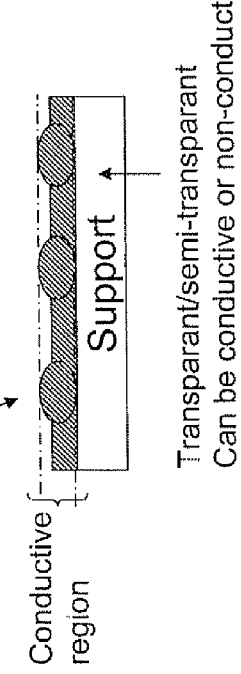
Fig. 27 (cont.)

METHOD AND APPARATUS FOR DETECTING AN ANALYTE

CROSS REFERENCE TO RELATED APPLICATIONS

This application claims the benefit of priority as a Continuation-in-Part of U.S. patent application Ser. No. 10/322,901, filed Dec. 18, 2002 now abandoned, which claims the benefit of priority of U.S. Provisional Patent Application Ser. No. 60/345,169, filed Dec. 21, 2001. This application also claims priority benefits as a Continuation-in-Part Application of U.S. patent application Ser. No. 11/175,729, filed on Jul. 5, 2005, which claims the benefit of priority of U.S. Provisional Patent Application Ser. No. 60/584,953, filed Jul. 2, 2004. The present application also claims the benefit of priority of U.S. Provisional Patent Application 60/733,277, filed Nov. 2, 2005.

The disclosures of U.S. patent application Ser. No. 10/322,901, U.S. Provisional Patent Application 60/345,169, U.S. patent application Ser. No. 11/175,729, U.S. Provisional Patent Application 60/584,953, and U.S. Provisional Patent Application 60/733,277 are incorporated by reference herein in their entirety.

BACKGROUND

I. Field of the Invention

This disclosure relates generally to assaying and, more specifically, to methods and apparatus for assaying an analyte.

II. Description of Related Art

Different types of biosensors are known, along with their specific advantages and disadvantages. For example, electrochemical biosensors, surface acoustic wave sensors and surface plasmon resonance biosensors are known biosensors that have the advantage of not requiring the use of labeling techniques for most applications. However, these sensors also have certain disadvantages.

A current method for assaying an analyte (e.g., antibodies and/or antigens) in a fluid sample is accomplished using surface plasmon resonance ("SPR") techniques. In such a technique, the presence of an analyte is determined by a change in the refractive index at a solid optical surface when the analyte interacts with a refractive index enhancing species, thereby causing binding or release of the species from the surface. In this respect, the SPR signal is a measure of mass concentration at a sensor chip surface. This means that the analyte/ligand association and dissociation in the sample can be observed and, ultimately, rate constants as well as equilibrium constants can be determined.

However, as was noted above, acquiring such SPR measurements has some disadvantages. In this respect, systems for carrying out such analyses are typically expensive as those systems generally employ a quartz prism as well as a radiation source that is capable of generating polarized light. Also, the response of an SPR sensor depends on the volume and refractive index of the bound analyte. Therefore, for very small molecules, this technique results in very small changes of refractive index and can make detecting such analytes difficult.

Another current approach for detecting an analyte is the use of an optical based sensing device for detecting the presence (and amount of) an analyte using both indicator and reference channels. The sensing device used in such an approach typically includes a sensor body with a radiation source contained therein. The radiation emitted by the source interacts with molecules in the material (i.e., the sample) being analyzed, which typically results in a change of at least one optical characteristic of those molecules. Such a change is not desirable as it may reduce the accuracy of information regarding the analyte obtained. Therefore, based on the foregoing, a need exists for improved methods and apparatus for assaying analytes.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with devices and methods which are given by way of example and meant to be illustrative, not limiting in scope. In various embodiments, one or more of the above-described problems have been reduced or eliminated, while other embodiments are directed to other improvements.

In a first aspect, the invention comprises a method for determining the concentration of an analyte within a sample, the method comprising:

providing a first substrate comprising a conductive region and a recognition layer, the conductive region having a first surface operatively coupled (i.e., in close proximity, in which the conductive region and recognition layer may be, for example, covalently coupled, coupled via linking molecules, or the recognition layer adsorbed on the conductive region) with the recognition layer, the recognition layer comprising at least one recognition molecule, wherein said conductive region comprises at least one particle and wherein the distance between the first surface of the conductive region and the recognition molecule is selected such that when the analyte is bound to the recognition layer the combination of the at least one particle and the analyte exhibits at least one of the following effects when radiation is directed through the conductive region and the recognition layer: (i) a particle plasmon effect, (ii) a particle bulk interband absorption, (iii) analyte molecular absorption, and (iv) absorption by the analyte-particle combination;

contacting the substrate with the sample to bind at least some of any analyte present in the sample with the recognition molecule;

directing radiation through the conductive region and the recognition layer, measuring at least a part of a spectrum of radiation that is absorbed or transmitted by or through the substrate, the at least part of the spectrum manifesting at least one of (i) a particle plasmon effect, (ii) a particle bulk interband absorption, (iii) an analyte molecular absorption and (iv) an absorption by the analyte-particle combination;

comparing the at least part of the spectrum with a reference spectrum and determining the difference; and determining the concentration of the analyte from the difference.

In a preferred embodiment of the first aspect of the invention, the distance between the first surface and the recognition molecule is less than 60 nm.

The distance between the first surface of the conductive region and the recognition molecules is preferably selected such that it is less than 60 nm, less than 50 nm, less than 40 nm, less than 30 nm or less than 25 nm, less than 20 nm, less than 15 nm or even less than 10 nm. In one embodiment the distance is less than 17 nm, preferably between 4 and 17 nm.

The distance between the recognition molecule and the first surface of the conductive region is selected such that at least one of effects (i) to (iv) is observed.

This allows more sensitive measurements because the transmission of light through the conductive region creates a surface plasmon resonance wave, the length of this wave decaying exponentially away from the conductive region. The surface plasmon resonance wave results in the effects (i) to (iv). The distance is measured from the first surface up to the part of the recognition molecule where the binding with the analyte takes place.

In a particular embodiment of the first aspect, the distance between the recognition molecule and the first surface is obtained by selecting the appropriate size of the recognition molecules. The recognition molecule will be positioned close to the first surface of the conductive region, meaning at a distance at least less than 60 nm, less than 50 nm, less than 40 nm, less than 30 nm, less than 25 nm less than 20 nm, less than 15 nm or even less than 10 nm from the first surface of the conductive region. The distance should be between 1 nm and 60 nm, between 1 nm and 50 nm, between 1 nm and 40 nm, between 1 nm and 30 nm, between 1 nm and 20 nm, between 1 nm and 10 nm, 5 nm and 40 nm, between 5 nm and 35 nm or between 5 nm and 25 nm. The recognition molecule can have a molecular weight less than 150 000 Dalton, less than 100 000 Dalton, less than 80 000 Dalton, less than 70 000 Dalton, less than 60 000 Dalton, less than 50 000 Dalton, less than 40 000 Dalton, less than 30 000 Dalton, less than 20 000 Dalton. In a preferred embodiment, the molecular weight is between 200 Dalton and 40 000 Dalton or even between 10 000 Dalton and 40 000 Dalton.

The recognition molecule can be a small molecule such as a hormone, peptide, or antibiotic. In other cases the recognition molecule can treated such that only the active part (the part that binds the analyte) of the recognition molecule is part of the recognition layer. In particular, the recognition molecule can be subjected to cleavage with enzymes such as proteases or chemical reducing agents such as dithiotreitol (Fab, Fab', (Fab')$_2$). The recognition molecule can be a single chain Fv fragment (ScFv). In another embodiment, the recognition molecule can be a recombinant camel antibody fragment (VHH).

In an embodiment of the first aspect, the invention comprises a method as recited in any of the previous embodiments of this invention is disclosed wherein the at least one particle exhibits a particle plasmon effect and a bulk interband absorption and a plasmon coupling band when analyte is bound to the recognition molecule.

In an embodiment of the first aspect, the invention comprises a method as recited in any of the previous embodiments wherein the at least one particle is formed of a material selected from the group consisting of diamond, a metal, a semiconductive material and combinations thereof.

In an embodiment of the first aspect, the invention comprises a method as recited in any of the previous embodiments wherein the at least one particle is an alloy of at least two metals.

In an embodiment of the first aspect, the invention comprises a method as recited in any of the previous embodiments wherein the at least one particle is formed of a semiconductive material.

In an embodiment of the first aspect, the invention comprises a method as recited in any of the previous embodiments wherein the at least one particle is formed of a core material and a shell material.

In an embodiment of the first aspect, the invention comprises a method as recited in any of the previous embodiments wherein the conductive region comprises semiconductive particles and metallic particles.

In an embodiment of the first aspect, the invention comprises a method as recited in any of the previous embodiments wherein the conductive region comprises at least two particles and the edge to edge distance of the at least two particles is between 1 nm and 5 µm, preferably between 1 nm and 1 µm.

In an embodiment of the first aspect, the invention comprises a method as recited in any of the previous embodiments wherein the conductive region is arranged such that when radiation is transmitted through the substrate, measuring an intensity of the radiation absorbed or transmitted by or through the substrate is performed in a wavelength region between 200 nm and 1200 nm.

In an embodiment of the first aspect, the invention comprises a method as recited in any of the previous embodiments wherein the average diameter of the at least one particle is smaller in dimension than a principal wavelength of the radiation.

In an embodiment of the first aspect, the invention comprises a method as recited in any of the previous embodiments wherein the average diameter of the at least one particle is less than 300 nm.

In an embodiment of the first aspect, the invention comprises a method as recited in any of the previous embodiments wherein an interaction between the analyte and the recognition layer results in a change in a dielectric constant of the recognition layer.

In an embodiment of the first aspect, the invention comprises a method as recited in any of the previous embodiments wherein the substrate further comprises a support layer and a second surface of the conductive region, the second surface being operatively coupled with the support layer.

In an embodiment of the first aspect, the invention comprises a method as recited in any of the previous embodiments wherein the support layer is optically transparent to the radiation. In such embodiments, one measures the radiation that is transmitted through the layer and the substrate, and, therefore, the substrate is (semi-)transparent for the wavelength that is used. In another embodiment of the first aspect, the invention comprises a method as recited in any of the previous embodiments the substrate is a least partially reflective, and one measures the reflectance.

In an embodiment of the first aspect, the invention comprises a method as recited in any of the previous embodiments wherein the support layer is optically transparent or semi-transparent to the radiation. By "semi-transparent" is meant that less than 100% transparent but that enough light can be transmitted through the substrate to be able to measure the transmission.

In an embodiment of the first aspect, the invention comprises a method as recited in any of the previous embodiments wherein the recognition layer comprises an intermediate layer (between 0.5 nm and 3 nm thick) and a recognition molecule. The recognition molecule may be associated with the intermediate layer in any manner that immobilizes the recognition molecule in, on, or connected to the intermediate layer.

In an embodiment of the first aspect, the invention comprises a method as recited in any of the previous embodiments wherein the recognition layer comprises a self-assembling monolayer as an intermediate layer.

In general, any layer that can immobilize the analyte, thereby showing a plasmon effect, can be used. A self-assembling monolayer is but one example of a layer that "operatively" can couple the recognition molecule to the conductive region. Self-assembling monolayers provide the following advantages:

1) Self-assembled monolayers ("SAMs") with reactive groups such as thiols can attach covalently via the reactive (e.g., thiol group) to the conductive region (e.g., to nobel metal nanoparticles) and are thus stable;
2) SAMs generally have limited thickness, making it possible to detect closer to the conductive region (e.g., nanoparticle) surface;
3) SAMs allow the integration of chemical groups that can be used to covalently attach the biomolecules onto the conductive region surface (e.g., nanoparticle film) and enable control of binding events, such as bind specificity, thereby making detection reproducible.

In an embodiment of the first aspect, the invention comprises a method as recited in any of the previous embodiments wherein the substrate comprises a plurality of conductive regions, the plurality of conductive regions being arranged in an array.

In an embodiment of the first aspect, the invention comprises a method as recited in any of the previous embodiments wherein the substrate is arranged as a microtitre plate.

In an embodiment of the first aspect, the invention comprises a method as recited in any of the previous embodiments wherein an intensity of the radiation absorbed or transmitted by or through the substrate is determined as a function of a wavelength of the radiation.

In an embodiment of the first aspect, the invention comprises a method as recited in any of the previous embodiments wherein instead of comparing at least a part of a spectrum of radiation that is absorbed or transmitted by or through the substrate with a reference spectrum, the method comprises:

providing a second substrate, which comprises a conductive region and no recognition layer or a recognition layer that comprises molecules having no analyte binding capacity or non-specific binding capacity;

subjecting the second substrate to an analyte-containing reference sample directing radiation through the second substrate;

measuring the intensity of the radiation absorbed or transmitted by or through the second substrate; and comparing an intensity of the radiation absorbed or transmitted by or through the second substrate with an intensity of the radiation absorbed or transmitted by or through the first substrate to determine the concentration of the analyte on the first substrate.

In this embodiment, the signal observed with the second substrate can be subtracted from the signal of the sample with specific receptor molecules for the analyte of interest. A third substrate can also be used in conjunction with the second substrate, wherein the third substrate comprises the same recognition molecules as in the first substrate, the third substrate is subjected to a sample without analyte, and the transmission/adsorption is measured and subtracted from the measurements of the first substrate.

In an embodiment of the first aspect, the invention comprises a method as recited in any of the previous embodiments wherein the conductive region comprises at least two particles and a combination of the at least two particles and the analyte further exhibits a plasmon coupling effect.

An example method for analyzing and determining the presence of an analyte within a sample is disclosed. In one embodiment, such a method includes providing a substrate having a conductive region and a recognition layer. The conductive region of the substrate has at least two surfaces, a first surface and a second surface, wherein the first surface is operatively associated with the recognition layer. The recognition layer of the substrate is contacted with the analyte so that a reaction occurs between the analyte and the recognition layer. As used herein, a "reaction" is any binding event which immobilizes the analyte on, near, or to the recognition layer. The recognition layer comprises at least one recognition molecule, which can bind with the analyte. After this reaction, radiation is directed through the conductive region and the recognition layer. By measuring the intensity of the radiation absorbed and/or transmitted by the substrate as a function of the radiation's wavelength, the presence of an analyte can be determined. The method also can be used generally for affinity immunosensing and biosensing. For instance, by optically monitoring the recognition layer, one may detect the presence of antigens captured by surface immobilized antibodies.

Further in this embodiment, the conductive region includes at least one particle, which has an average diameter that is preferably smaller than the wavelength of the impinging radiation. The interaction between the analyte and the conductive region affects the dielectric constant of the conductive region and the recognition layer, which results in a change in the absorption or transmittance spectrum of the substrate. Moreover, this interaction results in a change in plasmon resonance frequency, which is mainly determined by the dielectric function of the conductive region and the surrounding medium. For this arrangement, the surrounding medium includes the recognition layer and the conductive particle(s). The recognition layer may be, for example, a self-assembling monolayer. FIG. 26 displays an example of a mixed SAM, but other suitable SAM's may be used as well. Other examples include polymers and silanes that can be used to immobilize the receptor molecules on the substrate.

In certain embodiments, the average diameter of the conductive particle(s) is (are), alternatively less than 300 nm, less than 200 nm, less than 100 nm or less than 50 nm, depending on the particular application and the specific analyte being assayed. The conductive region may include a metal on which a plasmon effect can be induced. For example, such a metal may be selected from the group consisting of gold, silver and copper.

In other embodiments, the substrate also further includes a support layer. In this arrangement, a second surface of the substrate is operatively coupled with the support layer, where the support layer is optically transparent or semi-transparent.

In still other embodiments, the substrate may have multiple conductive regions, which are ordered in an array arrangement. For instance, the substrate may be a microtitre plate that is constructed so as to be used for high-throughput screening.

In another embodiment, a method for analyzing and determining the presence of an analyte within a sample includes providing a second substrate, where the second substrate includes a conductive region having at least a first surface and a second surface and a recognition layer, where a first surface of the conductive region is operatively coupled with the recognition layer. The method further includes subjecting the second substrate to a reference sample, then directing radiation through the conductive region and the recognition layer of the second substrate. The method still further includes measuring the intensity of the radiation absorbed and/or transmitted by the second substrate as a function of wavelength and comparing that intensity with the intensity of the radiation absorbed or transmitted by the first substrate. Using this comparison, the presence of an analyte can be determined.

Such techniques provide for assaying an analyte without labeling, where such techniques are relatively sensitive, as compared with prior techniques. Furthermore, such techniques are less complex and have lower cost than current approaches. Such techniques may be used, for example, for assaying biomolecules.

In another aspect, the invention comprises a substrate as described above in any of the embodiments of the methods described above. In a preferred embodiment, in the substrate described hereinabove, the distance between the first surface of the conductive region and the recognition molecules is preferably selected such that it is less than 60 nm, less than 50 nm, less than 40 nm, less than 30 nm or less than 25 nm, less than 20 nm, less than 15 nm or even less than 10 nm. The distance between the recognition molecule and the first surface of the conductive region is selected such that upon binding of an analyte to the recognition molecule at least one (i) a particle plasmon effect, (ii) a particle bulk interband absorption, (iii) analyte molecular absorption, and (iv) absorption by the analyte-particle combination may be observed.

In this aspect, the invention comprises a substrate for determining the concentration of an analyte within a sample, the substrate comprising:

a conductive region and a recognition layer, the conductive region having a first surface operatively coupled with the recognition layer, the recognition layer comprising at least one recognition molecule, wherein said conductive region comprises at least one particle and wherein the distance between the first surface of the conductive region and the recognition molecule is selected such that when the analyte is bound to the recognition layer the combination of the at least one particle and the analyte exhibits at least one of the following effects when radiation is directed through the conductive region and the recognition layer: (i) a particle plasmon effect, (ii) a particle bulk interband absorption, (iii) analyte molecular absorption, and (iv) absorption by the analyte-particle combination;

wherein the distance between said first surface and the part of said recognition molecule where binding takes place is less than 60 nm.

In preferred embodiments of this aspect of the invention:
a) the distance between said first surface and the part of said recognition molecule where binding takes place is less than 17 nm;
b) the distance between said first surface and the part of said recognition molecule where binding takes place is between 4 and 17 nm;
c) the recognition molecule is subjected enzymatic cleavage such that only the active part of the recognition molecules is part of the recognition layer;
d) the recognition molecule is a small molecule that functions as a recognition element in an inhibition or replacement assay;
e) the at least one particle exhibits a particle plasmon effect and a bulk interband absorption and a plasmon coupling band;
f) the at least one particle is formed of a material selected from the group consisting of diamond, a metal, a semiconductive material and combinations thereof;
g) the at least one particle is an alloy of at least two metals;
h) the at least one particle is formed of a semiconductive material;
i) the at least one particle is formed of a core material and a shell material;
j) the conductive region comprises semiconductive particles and metallic particles;
k) the conductive region comprises at least two particles and the edge to edge distance of the at least two particles is between 1 nm and 5 µm;
l) the conductive region comprises at least two particles and the edge to edge distance of the particles is between 1 nm and 1 µm;
m) the conductive region is arranged such that when radiation is transmitted through the substrate, measuring an intensity of the radiation absorbed or transmitted by or through the substrate is performed in a wavelength region between 200 nm and 1200 nm;
n) the average diameter of the at least one particle is smaller in dimension than a principal wavelength of the radiation;
o) the average diameter of the at least one particle is less than 300 nm;
p) an interaction between the analyte and the recognition layer results in a change in a dielectric constant of the recognition layer;
q) the substrate further comprises a support layer and a second surface of the conductive region, the second surface being operatively coupled with the support layer, preferably wherein (i) the support layer is optically transparent to the radiation or (ii) the support layer is optically semi-transparent to the radiation;
r) the recognition layer comprises an intermediate layer and a recognition molecule;
s) the recognition layer comprises a self-assembling monolayer;
t) the substrate comprises a plurality of conductive regions, the plurality of conductive regions being arranged in an array;
u) the substrate is arranged as a microtitre plate;
v) the conductive region comprises at least two particles and a combination of the at least two particles and the analyte further exhibits a plasmon coupling effect.

In another aspect, the invention comprises an apparatus/device for conducting the method as described hereinabove. Such an apparatus comprises a light source for illuminating a substrate, a substrate as described hereinabove, and a light detection device for detecting the intensity of radiation from the light source absorbed or transmitted by or through the substrate.

We have found that the plasmon resonance signal is higher/better/more reliable when the distance between the particles and the conducting substrate is smaller, as described here and above. Having a smaller distance enhances sensitivity and permits detection and quantification of smaller analyte concentrations.

BRIEF DESCRIPTION OF THE DRAWINGS

Example embodiments are illustrated in referenced figures of the drawings. It is intended that the embodiments and figures disclosed herein are to be considered illustrative rather than restrictive.

DETAILED DESCRIPTION

Overview

The methods of the invention for detecting an analyte can be used, for example, in conjunction with sensing devices that have a high sensitivity and that can be used to detect very low concentrations of certain analytes. In particular, such a method may be used for affinity immunosensing and biosensing. Such a method may include optically monitoring the deposition of an intermediate layer or linking layer (the terms "intermediate layer" and "linking layer" are used interchangeably herein), recognition of an immobilized recognition molecule such as antibody, antigen, enzyme, cells hormone, peptides, receptor molecules and nucleic acid, and recognition of the analyte, which involves optically monitoring for recognition of the analyte (e.g., antigen) by an immobilized receptor molecule (e.g., antibody). The method is versatile, and allows for applications in both the liquid and gas phases, while also allowing for quantitative in situ measurements.

More specifically, a method for assaying an analyte in a sample (e.g., a liquid sample) may be accomplished by bringing the sample into physical contact with a substrate, where the substrate includes a conductive region and a recognition layer. The presence of the analyte (in the sample) being assayed is then determined by a resulting change in the spectrum (wavelength/frequency vs. intensity) of radiation transmitted through the substrate (or absorbed by the substrate) resulting from the presence (or non-presence) of the analyte (e.g., as compared with a reference spectrum where no analyte is present).

For purposes of this disclosure, it should be understood that the terms "absorbed radiation (or absorbance)" and "transmitted radiation (or transmittance)" can be used interchangeably. In this respect, the relationship between the absorbance (A) and the transmittance (T) may be given by the equation: $A = -\log T$.

Exemplary Apparatus for Assaying an Analyte

Figure 1:
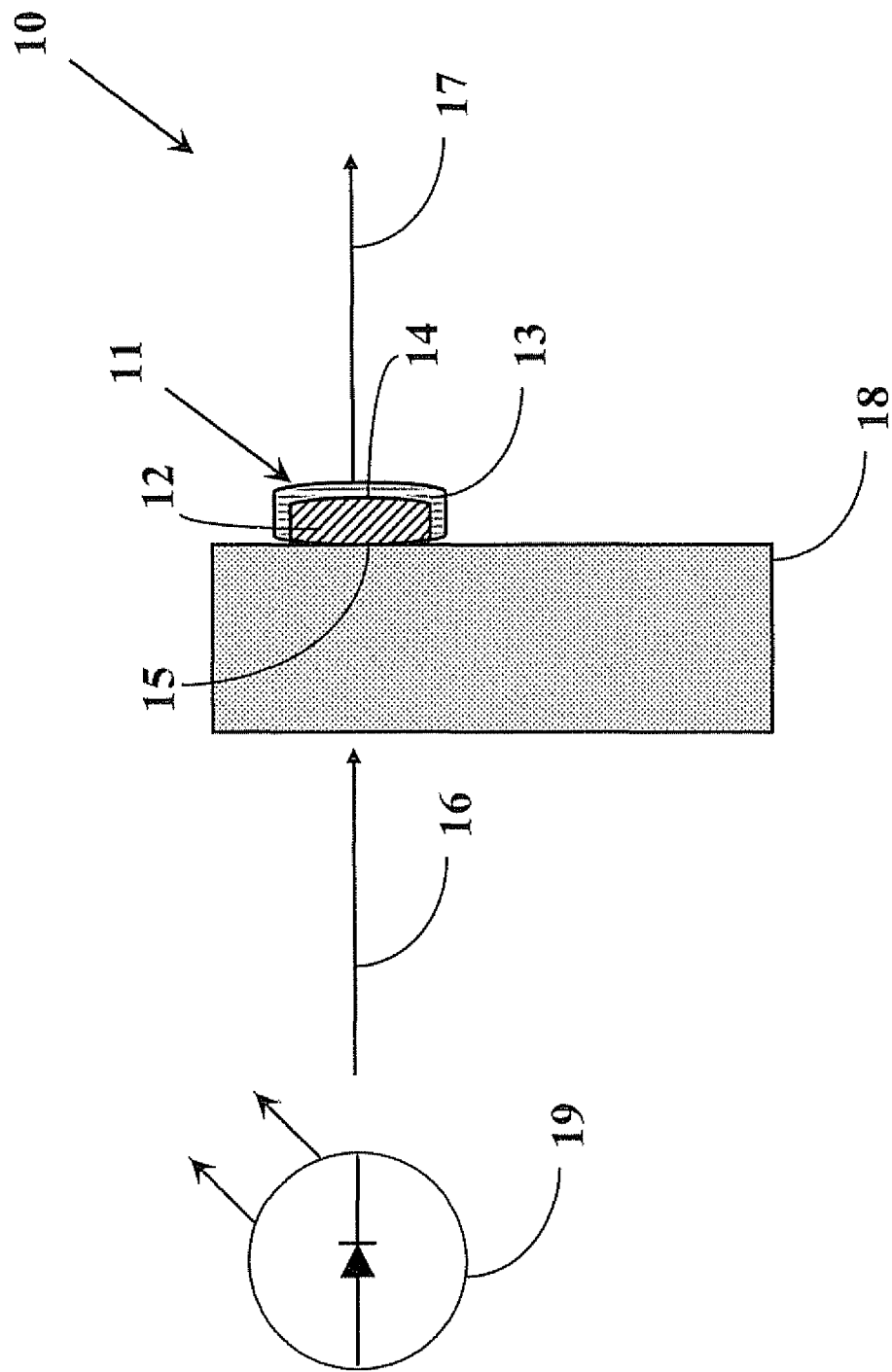
FIG. 1 is a drawing illustrating an experimental apparatus for detecting an analyte.

Referring now to FIG. 1, a drawing illustrating an exemplary embodiment of an experimental apparatus 10 for assaying an analyte in a sample is shown. The apparatus 10 includes a substrate 11. The substrate 11 has a conductive region 12 and a recognition layer 13. The conductive region 12 has a first surface 14 and a second surface 15, where the first surface 14 is operatively coupled with the recognition layer 13.

When the substrate 11 is subjected to (e.g., placed in physical contact with) a sample containing the analyte (not shown), an interaction (if the analyte is present) occurs between the analyte and the recognition layer 13. After such an interaction has occurred, radiation 16 is directed through the substrate 11, such that the radiation 16 is incident with the conductive region 12 and the recognition layer 13. The presence and/or concentration of the analyte in the sample is then determined by measuring the intensity (or amount) of the radiation 16 that is absorbed by (or transmitted through) the substrate 11. This measurement is a function of the wavelength of radiation 17 (e.g., the radiation that is communicated through the substrate 11).

As shown in FIG. 1, the substrate 11, for this embodiment, further comprises a support layer 18, where the second surface 15 of the conductive region 12 is operatively coupled with the support layer 18 using a molecular glue of for example a SAM of mercapto-silanes; The support layer 18 provides mechanical support to the substrate 11 and facilitates subjecting the substrate 11 to samples being assayed using the substrate 11; By "operatively coupled" we mean that the second surface of the conductive region and the support layer are in close proximity (e.g., covalently linked, one adsorbed on another, coupled via linking molecules, etc.).

The radiation 16 shown in FIG. 1 may be generated by any number of radiation sources such as (without limitation) an incandescent lamp, a light emitting diode (LED) or a laser. In the exemplary embodiment, a radiation source 19 for producing the radiation 16 preferably supplies the radiation 16 with a principal wavelength in the range corresponding to a maximum absorbance (or a minimum transmittance) wavelength of the substrate. The maximum absorbance of the substrate or the maximum absorbance of the combination of substrate with analyte adsorbed thereto both can be used. Often only the maximum absorbance of the substrate is known, however. In that case only the maximum absorbance of the substrate can be used. If known, it may be preferable to use the maximum absorbance of the combination of the substrate with the analyte adsorbed thereto. For instance, the radiation source 19 may provide the radiation 16 with a principal wavelength between 200 nm and 1500 nm.

For the apparatus 10, the radiation source 19 can take the form of a light emitting diode ("LED"), such as a red LED or a blue LED. Of course, other sources of radiation may be used. Alternatively, for example, the radiation source 19 may take the form of a focused beam source (e.g., a laser) or may be a source that provides a broader spectrum of light. Also, in certain embodiments, it may be advantageous for the radiation source 19 to provide collimated radiation, which may be either monochromatic or polychromatic radiation.

Furthermore, the apparatus 10 may include additional components (which are not shown) such as one or more devices placed between the radiation source 19 and the substrate 11, such as to collimate the radiation 16. These devices include, but are not limited to optical lenses, slotted gates, and grated filters. Additionally, a radiation sensor is typically used for analyzing the radiation 17 that is communicated through the substrate 11. Such sensors include (also without limitation) commercially available UV-Vis spectrometers. Alternatively, such a sensor may take the form of an absorptiometers or a calorimeter.

As previously discussed, the apparatus 10 shown in FIG. 1 includes the support layer 18, which provides mechanical support to the substrate 11. The support layer 18 is typically optically transparent or semi-transparent with regard to the principal wavelength of the radiation 16 provided by the radiation source 19. For example, the support layer 18 should have an optical transparency between 5% and 95%, with a transparency between 20% and 80% being preferable in certain applications. To provide this optical transparency, the support layer 18 may be formed using materials such as glass, quartz, or a polymeric material (such as polycarbonate, polysulphonate and polymethyl-methacrylate).

Depending on the material used to form the support layer 18, the support layer 18 may be flat. Alternatively, the support layer 18 may be part of a glass or quartz tube, a polymeric tube or a microtiter plate, which may be integrated in a flow system. The substrate 11 may also be a microtitre plate that is part of a high-throughput screening system or an apparatus for performing ELISA assay methods.

In an example embodiment, the conductive region 12 is formed of a material which exhibits one or more of (i) a particle (colloidal) plasmon effect, (ii) a bulk interband absorption effect and (iii) a plasmon coupling band effect. As was noted above, the first surface 14 of the conductive region 12 is operatively coupled with the recognition layer 12. Also, as shown in FIG. 1, the second surface 15 of the conductive region 12 is in contact with an external medium, in this case the support layer 18. Alternatively, the second surface 15 may be in air, or another gas.

In order to achieve one or more of the above effects, the particles of the conductive region 12 of substrate 11 may be formed of a conductive material, such as a conductive metal. In this respect, conductive region 12 may be formed from, for example, particles of gold, silver, or copper. However, it will be appreciated that the conductive region 12 may be formed from particles of any conductive material on which a plasmon effect can be induced. For example, the conductive region 12, alternatively, may be formed from particles of a conductive glass, conductive polymers or metallic nanoparticles. The conductive region 12 may also be formed of particles of diamond, a metallic material, a semi-conductive material or combinations thereof. As was noted above, the conductive region 12 includes at least one particle of the material selected for forming the conductive region 12.

Depending on the particular embodiment, the conductive region 12 may also be formed from particles of an alloy of at least two metals, which may be selected from the alloys Ag/Au, Si/Au, Si/Ag, Cu/Au, though other alloys are possible. In other embodiments, the conductive region 12 may be formed from particles of a combination of metallic materials and semi-conductive materials.

In other embodiments, the conductive region 12 may be formed from particles of (i) a semi-conductive material, (ii) a nanoshell or (iii) a combination of semi-conductive particles with metal particles and/or one or more metal alloy materials. For embodiment using semiconductive materials, such material may be selected such that conductive region demonstrates absorption characteristics from the low UV region to the VIS region to the near-IR region. Such materials include CdS, CdSe, PbS, PbSe, ZnS, CdTe, ZnSe, ZnTe, HgSe, HgS, HgTe, PbTe, and GaN, though other materials may also be appropriate in such an embodiment.

For embodiments using a nanoshell, the conductive region 12 may include particles of a core material and a shell material. Some example material combinations that may used to implement such nanoshells are (i) CdSe (core) and ZnS (shell); (ii) CdS (core) and ZnS (shell); (iii) CdSe (core) and Au (shell); (iv) CdSe (core) and Ag (shell); (v) CdS (core) and Au (shell); (vi) CdS (core) and Ag (shell); and (vii) ZnSe (core) and Au (shell). Of course, other material combinations are possible.

The conductive region 12 typically has a thickness of less than 60 nm, less than 50 nm, less than 40 nm, less than 30 nm, less than 20 nm, or less than 10 nm, with a thickness of less than 5 nm being preferable. Further in this regard, while the conductive region 12 is shown as being continuous in FIG. 1, alternatively the conductive region may be discontinuous, such that islands of conductive material are formed on the support layer 18, these islands having either uniform or non-uniform thickness.

With reference to FIGS. 27(A)-(E), in another embodiment the conductive region may comprise a support layer and a conductive layer comprised particles (as described herein), wherein the support layer is a semi-transparent or transparent substrate on/in which the conductive material is formed. The support layer can be conductive or non-conductive. The particles can be deposited on top of the substrate or can be incorporated in the substrate. The conductive material may be particles that are not connected, so form a discontinuous layer. The conductive layer may also be particles that are partially connected. The conductive layer may also be particles that are fully connected, but not fully covering the substrate. The conductive layer may also be particles that are connected and fully cover the substrate or support layer. The conductive layer may also be a uniform layer of conductive material. The particles can be randomly distributed over the substrate or can be arranged in a geometrical array. The particles may be homogenous or heterogenous in size. If heterogenous, the size may show a distribution such as Gaussian. The particles may be made of one material or a combination of particles of different materials can be used. In fact, any material that can manifest a surface Plasmon effect can be used. Also, polymer particles embedded in a conductive material (for example Au) showing surface Plasmon effect can be used.

The conductive material can be deposited by any deposition method known in the art, such as sputter deposition, PVD CVD, plating. Particles can be formed by evaporating a thin non-continuous layer. Particles can also be put on the substrate. Particles can also be made by evaporating a conducting layer on the substrate and consequently patterning in a well-defined pattern thereby creating isolated islands of the conducting material.

As an alternative to using a single particle to form the conductive region 12, the conductive region 12 may be formed of a plurality of particles. In such an embodiment, the conductive region 12 may be formed using a plurality of particles that are spaced in such a way that the particles exhibit an appropriate surface plasmon absorption spectrum for use in detecting the presence and/or concentration of an analyte. The edge-to-edge distance of such particles (e.g., the inter-particle distance) on the surface of the conductive region 12 can vary from 1 nm to several µm. An inter-particle spacing of 5 to 500 nm is typical for certain materials.

In the apparatus 10 shown in FIG. 1, the conductive region 12, as previously described, typically includes conductive particles and, more particularly, microparticles or nanoparticles, as such particles are smaller in molecular size than the preferable wavelength of the radiation 16 that impinges on the particles (and the substrate 11). The average diameter of these particles is typically less than 500 nm and, in certain embodiments, preferably less than 300 nm. The thickness of the conductive region 12 may also be less than 200 nm, less than 100 nm, less than 80 nm, less then 50 nm, less than 40 nm, less than 30 nm or less than 20 nm.

The size of the particles that form the conductive region 12 is dependent on the material selected for the conductive region 12 and the particular deposition process with which the conductive region 12 is formed. The shape of the particles that form the conductive region 12 may be, for example, spherical, but other structural and spatial configurations are possible. For instance, the particles may be slivers, cubes, ellipsoids, tubes, star-like, or take any number of other forms. In such instances, the size of a particle is defined as the smallest sphere encompassing it In certain embodiments, the particles used to form the conductive region 12 are hollow. As was previously noted, these particles are typically intrinsically conductive. However, the particles may also be formed from a polymeric material and then covered with a conductive material, such as the conductive materials described above.

Additionally, the conductive region 12 is typically formed in such a way so as to be optically tunable. In this context, optically tunable means that the conductive region 12 is produced in such a way so as to have a predetermined thickness or a predetermined particle size, where the thickness and/or particle size corresponds to a known value of the principal wavelength of the radiation 16. For instance, evaporation, sputtering, electroless plating or electroplating may be used to control the thickness of the conductive region 12.

As shown in FIG. 1, the second surface 15 of the conductive region 12 is operatively coupled with the support layer 18. For the apparatus 10, the second surface 15 of the conductive region 12 is deposited directly on the support layer 18. As an alternative, at least one adhesion layer (not shown) may be present between the support layer 18 and the second surface 15 of the conductive region 12. Such an adhesion layer may improve the stability of the conductive region 12. The adhesion layer(s) may be formed using, without limitation, a layer of self-assembling molecules, such as silane-based molecules or thiol-based molecules. See FIG. 26: example of thiol SAM. Furthermore, the adhesion layer(s) may also comprise a layer of organic linker molecules (e.g. an adhesive). It is noted that the adhesion layer may, but does not necessarily, have an effect on the absorption/transmittance characteristics of the conductive region 12. In certain situations it is preferable that such adhesion layers are non-metallic (i.e., non-conductive).

As was previously discussed, the recognition layer 13 is operatively coupled with the first surface 14 of the conductive region 12. The recognition layer 13 is a layer that includes, at a minimum, recognition, or receptor, molecules. The receptor molecules act as one part of a binding pair, while the analyte acts as the complementary component of the binding pair. Such binding pairs include, but are not limited to, antigen/antibody, enzyme/substrate, metal/chelator, bacteria/receptor, virus/receptor, hormone/receptor, hormone/antibody, antibiotic/antibody, and nucleic acid/nucleic acid (wherein the nucleic acids are independently DNA, RNA, or mixtures thereof and wherein the nucleotides may be independently modified at the base, sugar, and/or internucleoside linkage positions, as are well known in the art) pairs. Thus, the receptor molecules of the recognition layer 13 should have high specificity for the analyte being assayed. As was discussed above, such an interaction may result in a change of the dielectric constant of both the conductive region 12 and the recognition layer 13 and therefore, the substrate 11.

Alternatively, the recognition layer 13 may be a layer of cells that are deposited directly on the conductive region 12 or on an intermediate layer, such as an adhesion layer. For the exemplary embodiment shown in FIG. 1, such an intermediate layer should be understood as being formed on the first surface 14 of the conductive region 12. The recognition layer 13 may be designed such that non-specific binding or adsorption is substantially avoided.

The intermediate layer may be a self-assembling monolayer and can be formed on the conductive region 12 before binding with the first surface 14 of the substrate 11. For a conductive region 12 comprising an intermediate layer, the conductive region 12 may be bound directly to the first surface 14 of the substrate 11. Alternatively, the first surface 14 of the substrate 11 may be coated with chemical molecules that react (covalently or by physical adsorption) with the intermediate layer The recognition layer 13 may be formed using a self-assembled monolayer (SAM), on which the molecules of the recognition layer 13 can be bound (covalent or physical adsorption). Such a SAM, with a thickness of 0.5 to 3 nm, may include at least two functional groups. The first functional group may be selected such that it operatively couples with the first surface 14 of the conductive region 12. The second functional group may, as was noted above, be selected such that it interacts specifically with the analyte being assayed. The second functional group may also be selected such that it reacts with a recognition molecule. An interaction between the recognition molecules and the analyte may, but does not necessarily have to, result in a change of the absorption spectrum of the substrate 11. In certain embodiments, a SAM may be formed on the conductive region 12 before binding the conductive region 12 to the first surface 14 of the substrate 11.

Method for Assaying an Analyte

The apparatus 10, shown in FIG. 1, can be employed to implement a method to assay an analyte in a sample, as has been previously discussed. The analyte may be any one of various types of molecules such as, but not limited to, biomolecules, chemical ions, and other types of cells. More specifically, and again without limitation, such biomolecules include, but are not limited to, hormones, proteins (such as antibodies), antigens, steroids, nucleic acids, drug metabolites or micro-organisms. The sample can also be a "blank" sample, such as a liquid sample without analyte, or the substrate may be analyzed without being subjected to a sample, which may be useful for correlation or determining a reference spectrum, for example.

Such a method for assaying an analyte (still with reference to FIG. 1) may include subjecting the substrate 11 to a sample to be analyzed for the presence and/or concentration of the analyte. The substrate 11 is then subjected to the radiation 16 produced by the radiation source 19 such that the radiation 16 impinges on the substrate 11 and, in particular, on the conductive region 12 and the recognition layer 13. The transmittance, or the absorbance, is then determined from the radiation 17 that is communicated through the substrate 11.

Determining the transmittance, or absorbance, is typically done using a predetermined wavelength (e.g., the principal wavelength of the radiation 16). While such a measurement could be made by measuring a change in peak in the spectrum of radiation 17 over time, the transmission or absorption may also be determined by any change of the integrated area under the curve plotting the peak spectrum or, alternatively, by simply measuring a shift in the spectrum. For instance, the measured transmittance or absorbance gives an indication of the presence of an analyte in the sample because, when an analyte is present, the absorbance can increase or can decrease causing the spectrum to change. It will be appreciated that such spectrum changes depend on the specific materials used for the conductive region 12, the recognition layer 13, the support layer 18 and any adhesion (intermediate or linking) layers, as well as the interaction of these different layers, and on the particular analyte being assayed.

The transmittance, or absorbance, can be measured by a conventional absorptiometer (also referred to as a colorimeter) or spectrometer. The measurement of absorbance, or transmittance, is advantageous compared to fluorescence measurements because labeling of the analyte is not required. Consequently, this method is less complicated to conduct as compared to using current approaches. Furthermore, the use of a conventional light source, such as an LED, and the use of a conventional absorbtiometer may result in a lower cost process compared to current approaches. Additionally, the method may be performed in air, as "dry measurements" or, alternatively, in a solution (e.g., water based), such that a flow system can be used, which may be more versatile than current approaches.

Conventional ELISA Assay

Figure 2:
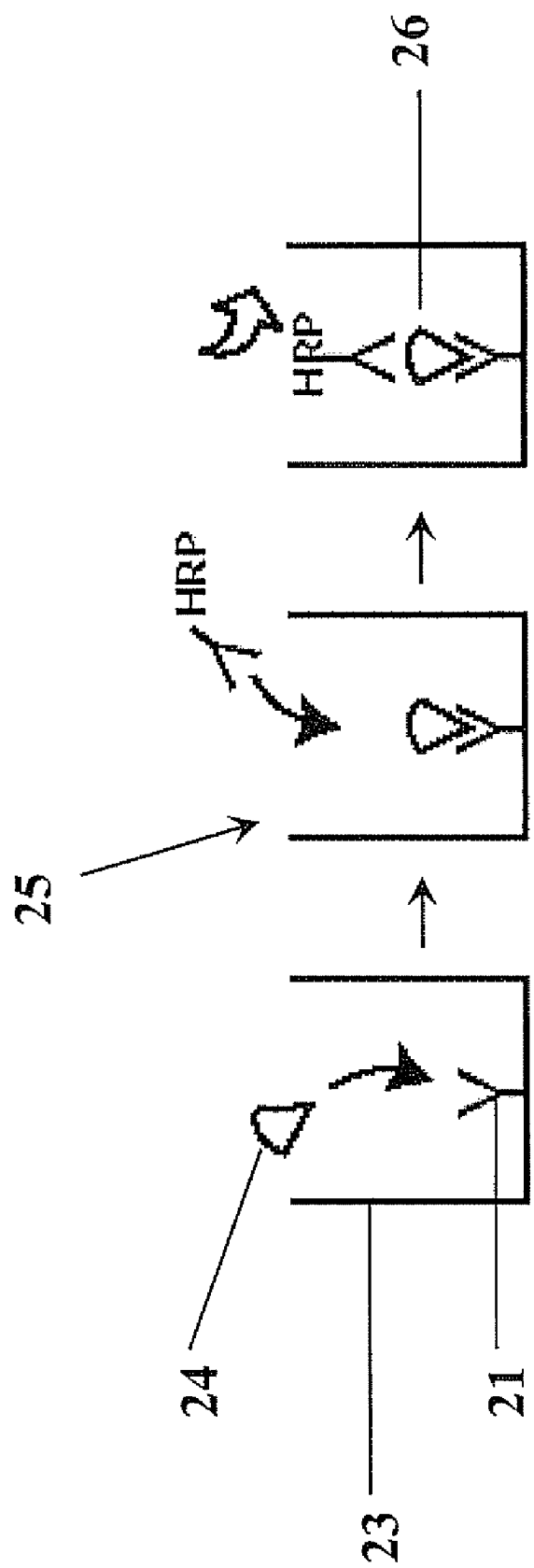
FIG. 2 is drawing illustrating a schematic representation of a conventional ELISA method of antigen detection.

FIG. 2 is a schematic representation of a conventional ELISA assay. The methods and apparatus described herein provide several advantages over such an approach, as will be discussed further below.

For this technique, as shown in FIG. 2, an antibody 21 is immobilized on a microtiterplate 23. However, the antibody 21 cannot be detected by conventional UV-Vis measurements, as may be done with the methods described herein. For the approach illustrated in FIG. 2, the detection limit of UV-Vis measurements is not adequate to detect a thin layer, or monolayer of proteins. In a next step, the analyte, or antigen 24 is recognized by the antibody 21. This event is also not visible by UV-Vis measurements, for similar reasons. Therefore, a secondary antibody 25 with a label, such as horseradish peroxidase ("HRP") is used to couple to the other side of the antigen 21, an event that is also not visible using UV-Vis measurements. In a next step an additional substance is added, which is converted by the HRP label to a color in a solution 26. The color is, or can give, a quantitative estimation of the amount of antigen in the sample. From this sequence of steps, dilution curves may be produced. Such dilutions curves typically require extensive development and complex calculations to be accurate. Therefore, such an approach is time consuming and costly.

In comparison, in a method such as those described herein, a thin layer of gold or nano-particles, for example, can be deposited on the bottom of a microtiterplate. The thin layer could be, in certain embodiments, gold nanoparticles. The thin layer will be referred to as gold particles hereinafter for the sake of simplicity, though it will be understood that particles of other metals (or alloys) can also be used. In a next step, the antibody is coupled to the gold particles. The absorbance of the gold particles coupled with the antibody is then measured. This measurement results in a background absorption spectrum. In a next step, the antibody is subjected to an external medium (e.g., a sample) containing an antigen to be detected. The antigen then interacts with the antibody, resulting in a change in the absorption spectrum. The change can be an increase in intensity, or a shift of the spectrum to lower/higher wavelengths. Consequently, the methods as described herein makes the assay process faster, simpler, less expensive, and more reliable.

Experimental Results

Protein Binding on Various Nanoparticle Films

In an experiment conducted using a method such as the one described above, ultra-thin gold films were prepared via evaporation and/or gold plating on mercaptosilanized glass or quartz substrates. The substrates were cleaned by placing them in 2 M NaOH for 2 hours, followed by a 7 min treatment with a 1:1:5 mixture of respectively $H_2O_2$ (30%), $NH_4OH$ (25%) and ultra-pure $H_2O$ at 80 to 90° C. in order to achieve a uniform, clean oxide layer.

3-Mercaptopropylmethyltrimethoxysilane was then dissolved in a 95:5 (v/v) solvent mixture at 2%. Then, self-assembled mercaptosilane adhesion layers were formed by immersing the substrates in this solution for up to 72 h. Following immersion, the substrates were removed from the solution and rinsed with methanol, blow-dried with $N_2$ and heated for 10 min at 110° C. The coated substrates were then stored in $N_2$ until gold evaporation or plating was performed.

For the preparation of the gold films, two techniques were used: (i) gold evaporation was performed at a speed of <5 Å/sec with an Alcatel SMC601. The final thickness on the mercaptosilanized substrates varied between 2 nm and 15 nm (average thickness) and (ii) electroless gold plating was performed as is described in Jin et al. (Jin, Y.; Kang, X.; Song, Y.; Zhang, B.; Cheng, G.; Dong, S. Anal. Chem. 2001, 73 (13), 2843).

The mercaptosilanized substrates were then immersed overnight in a colloidal gold solution. The substrates, having a monolayer of gold nanoparticles, were subsequently immersed in an aqueous 0.4 mM hydroxylamine hydrochloride and 0.1% $HAuCl_4.3H_2O$ solution. All glassware was cleaned with 2 M NaOH for 2 hours. The substrates varied in color from pink, to purple, to blue. This color variation is dependent on the plating time, and therefore film thickness. After plating, the substrates were rinsed thoroughly with water, dried under a nitrogen stream, and were then ready for preparation for assaying.

Self-assembled-monolayers (SAMs) of 16-mercapto-1-hexadecanoic acid ("16-MHA"), 1-octadecanethiol (HS-C18) and 1-dodecanethiol (HS-C12) were formed by immersing the clean ultra-thin gold substrates in a 1 mM thiol/ethanol solution for various periods of time. The substrates were then rinsed with ethanol and dried under a stream of $N_2$.

Figure 3:
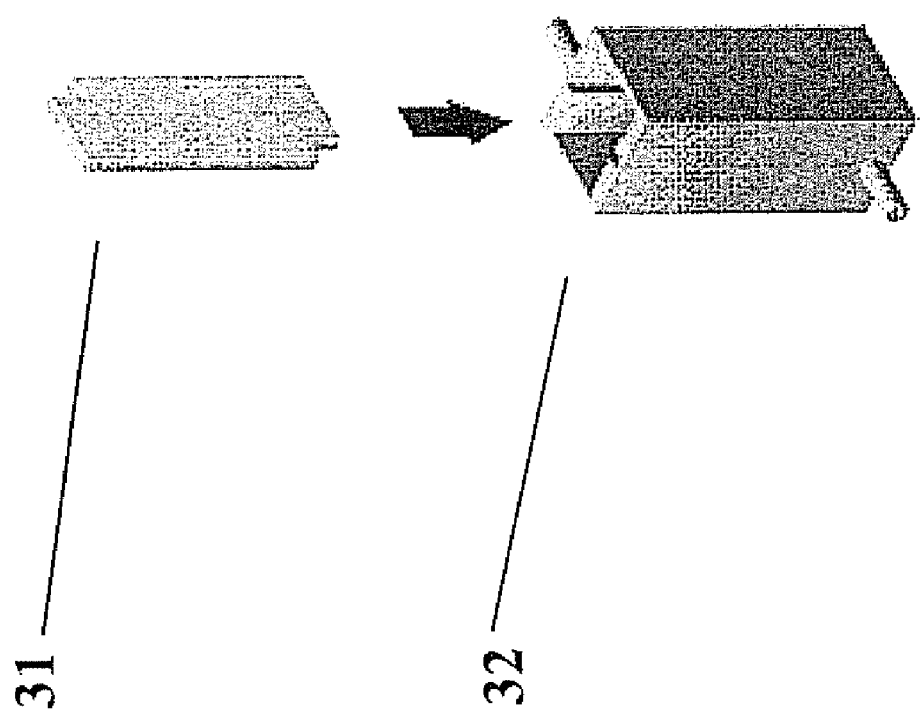
FIG. 3 is a drawing illustrating a schematic representation of slides and quartz cells that may be used to implement methods for detecting an analyte.

UV-Vis spectroscopic studies were carried out using a Shimatzu UV-1601PC with a slit width of 2 nm and a data interval of 0.5 nm. FIG. 3 is diagram illustrating an exemplary embodiment of a slide 31 (including one or more substrates) and a quartz cell 32 as described herein. Using UV-Vis measurement, the absorption spectra of the ultra-thin gold-coated slides 31 were measured in air by placing the slides 31 perpendicular to a light beam. Characterization in solution was then performed in the quartz cell 32, as shown in FIG. 3.

Surface images were then acquired in a tapping mode under ambient conditions using a PicoSPM manufactured by Molecular Imaging, USA. Silicon cantilevers having a spring constant between 1.2 and 5.5 N/m were used at resonant frequencies between 60 and 90 kHz.

Figure 4A:
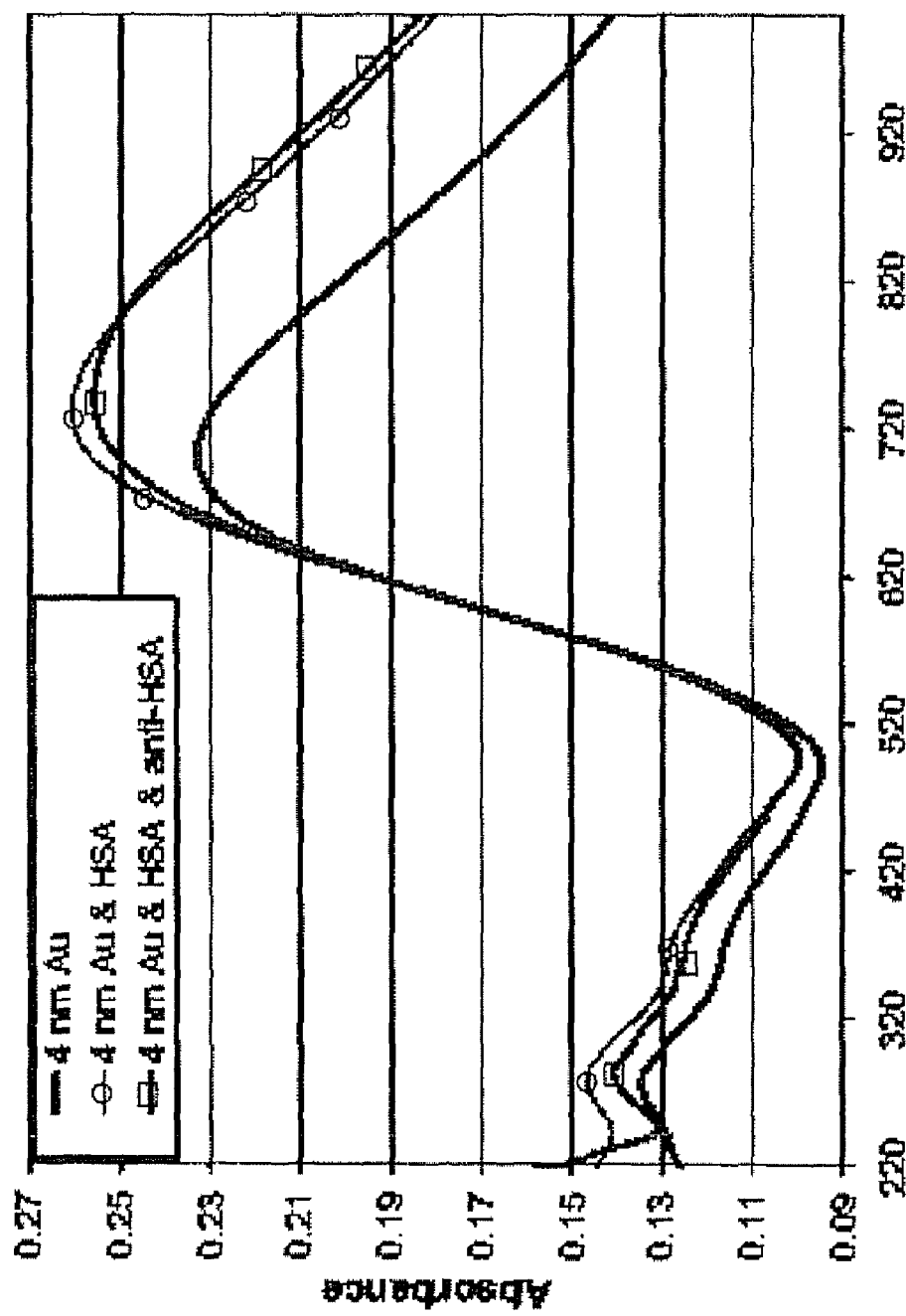
FIG. 4a is a graph illustrating absorbance spectra for (i) a thin gold film on quartz, (ii) deposited Human Serum Albumin ("HSA") on the thin gold film on quartz; and (iii) deposited HSA with subsequently deposited anti-HSA on the thin gold film on quartz.
Figure 4B:
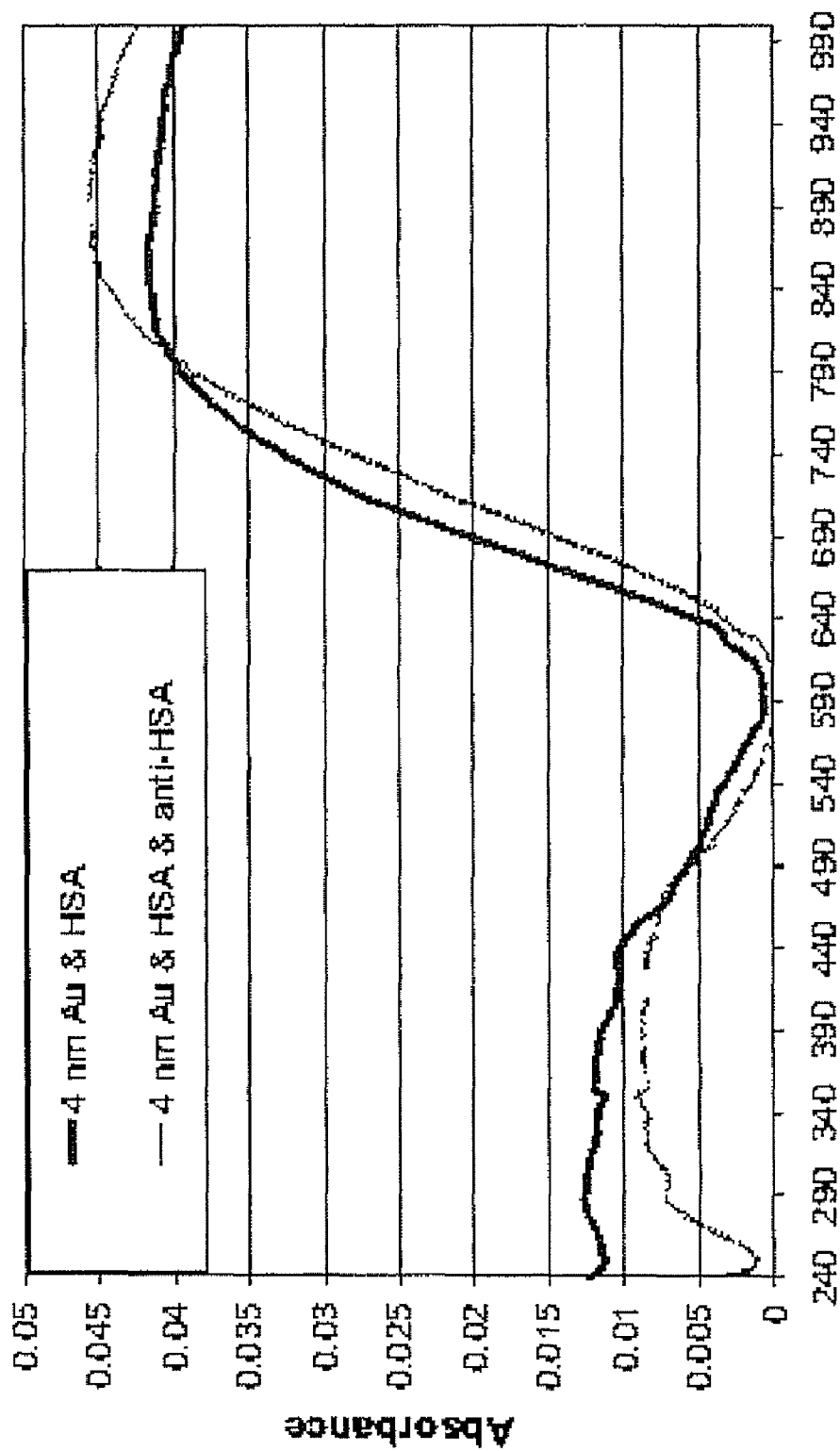
FIG. 4b is a graph illustrating difference spectra of the spectra of FIG. 4a (HSA and HSA+anti-HSA), which are background corrected for the absorbance spectrum of the thin gold film on quartz.

In a first experiment, Human Serum Albumin ("HSA") was directly absorbed on the thin gold film. FIG. 4a is graph illustrating absorbance spectra for such a substrate with HSA directly absorbed on an evaporated thin gold film. These measurements were taken at ambient conditions using a quartz substrate. FIG. 4b is graph illustrating difference spectra for HSA directly absorbed on an isolated thin gold film and for HSA directly absorbed on a thin gold film on quartz. These spectra are background-corrected, with the background being the absorbance spectra of the thin gold film.

The deposition of HSA on 4 nm of evaporated gold was performed by placing a drop of 1.244 mg/mL in PB for 120 min, followed by thoroughly rinsing with pure water and drying under a stream of $N_2$. The next step was the deposition of a drop of anti-HSA 250 µg/mL in PB for 180 min, with the same rinsing and drying procedure. The absorbance changes and shifts are shown after each biosensing step. The increase in peak height is a measure of the concentration of anti-HSA in the solution.

Self-assembled-monolayers of thiols were used to induce the absorption, or to covalently attach the bio-receptor molecules to the ultra-thin gold. In a next experiment, quartz with a 4 nm film of evaporated gold was used. The UV-Vis measurements were performed in air. The thin gold layer was immersed for 90 min in a 10 mM 1-dodecanethiol-ethanol solution. The absorption of HSA as a function of time was measured. Varying concentrations and times were used. The absorption was achieved using drops having varying concentrations of HSA in HBS.

Figure 5A:
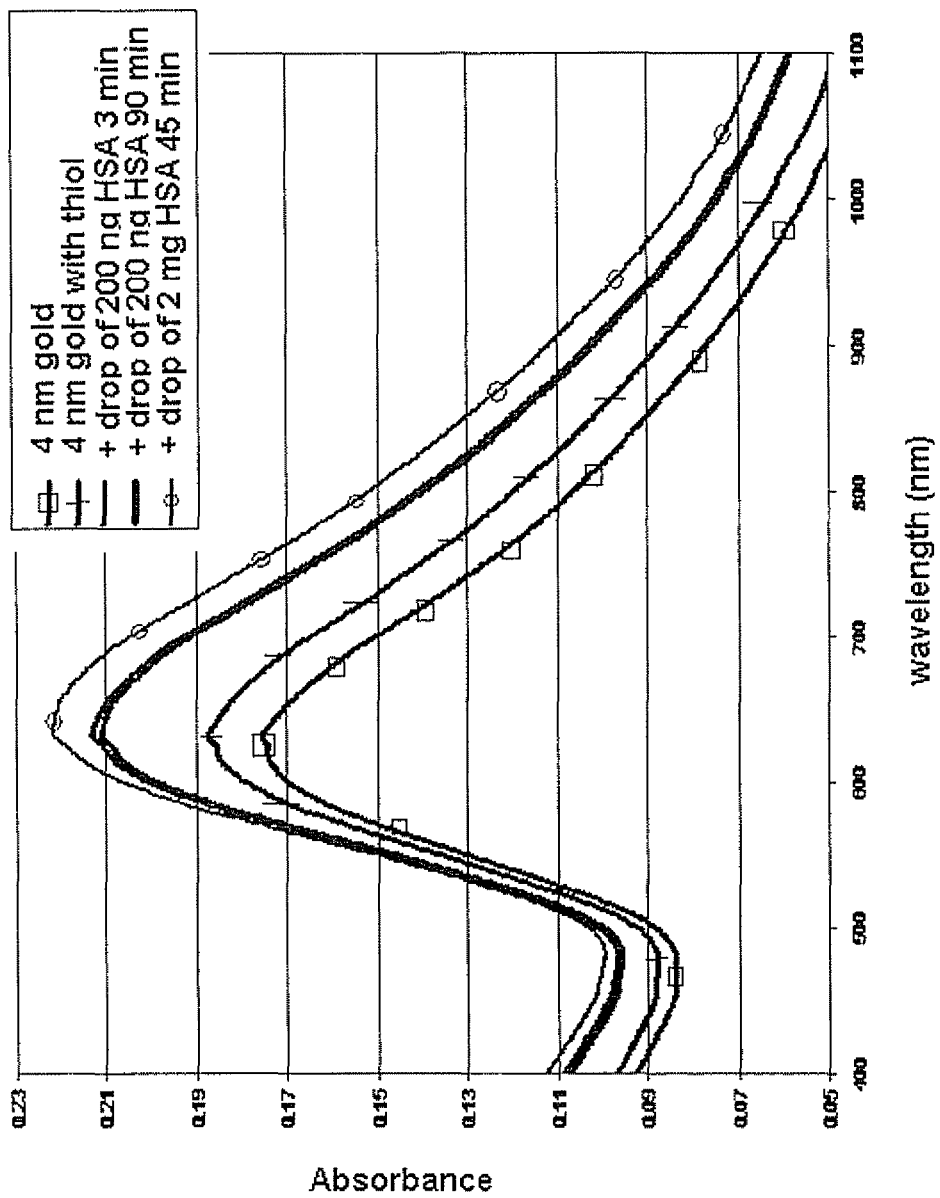
FIG. 5a is a graph illustrating absorbance spectra generated for (i) thin gold film; (ii) self-assembled monolayers of thiols on the thin gold film; and (iii) HSA at different concentrations and different deposition times on the thin gold film.
Figure 5B:
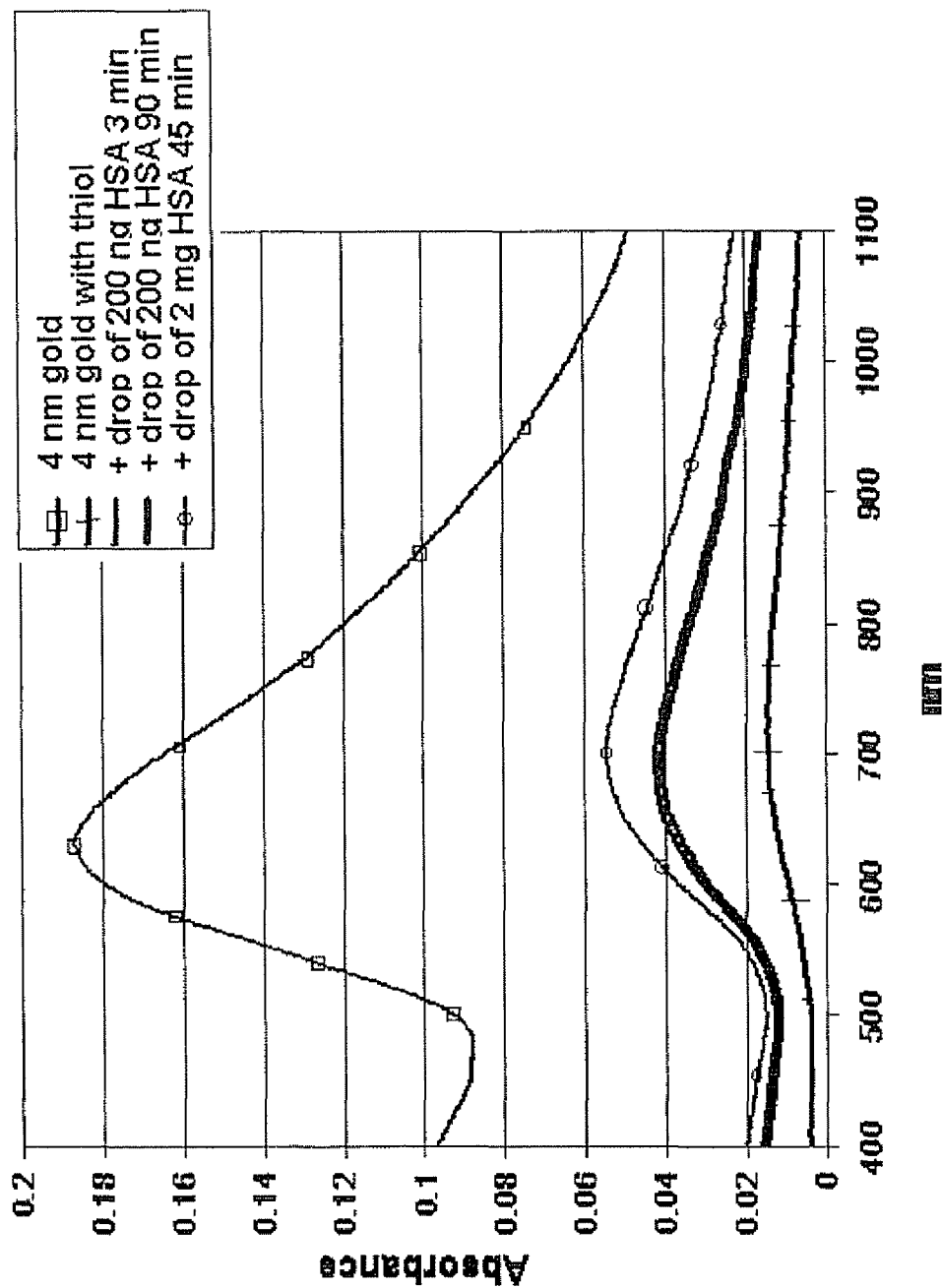
FIG. 5b is a graph illustrating difference spectra of the spectra of FIG. 5a (thiols and various HSA depositions), which are background corrected for the absorbance spectrum of the thin gold film.

FIG. 5a is a graph illustrating absorbance spectra of self-assembled-monolayers of thiols on gold followed by absorption of HSA at varying concentrations and periods of time. FIG. 5b is difference spectra of the spectra of FIG. 5a. The absorbance peak shift shown in FIG. 5a is more pronounced in the difference spectra in FIG. 5b. The dependence on the concentration of HSA is also clearly demonstrated by the increase in the absorbance after introducing higher concentrations of HSA.

Figure 6:
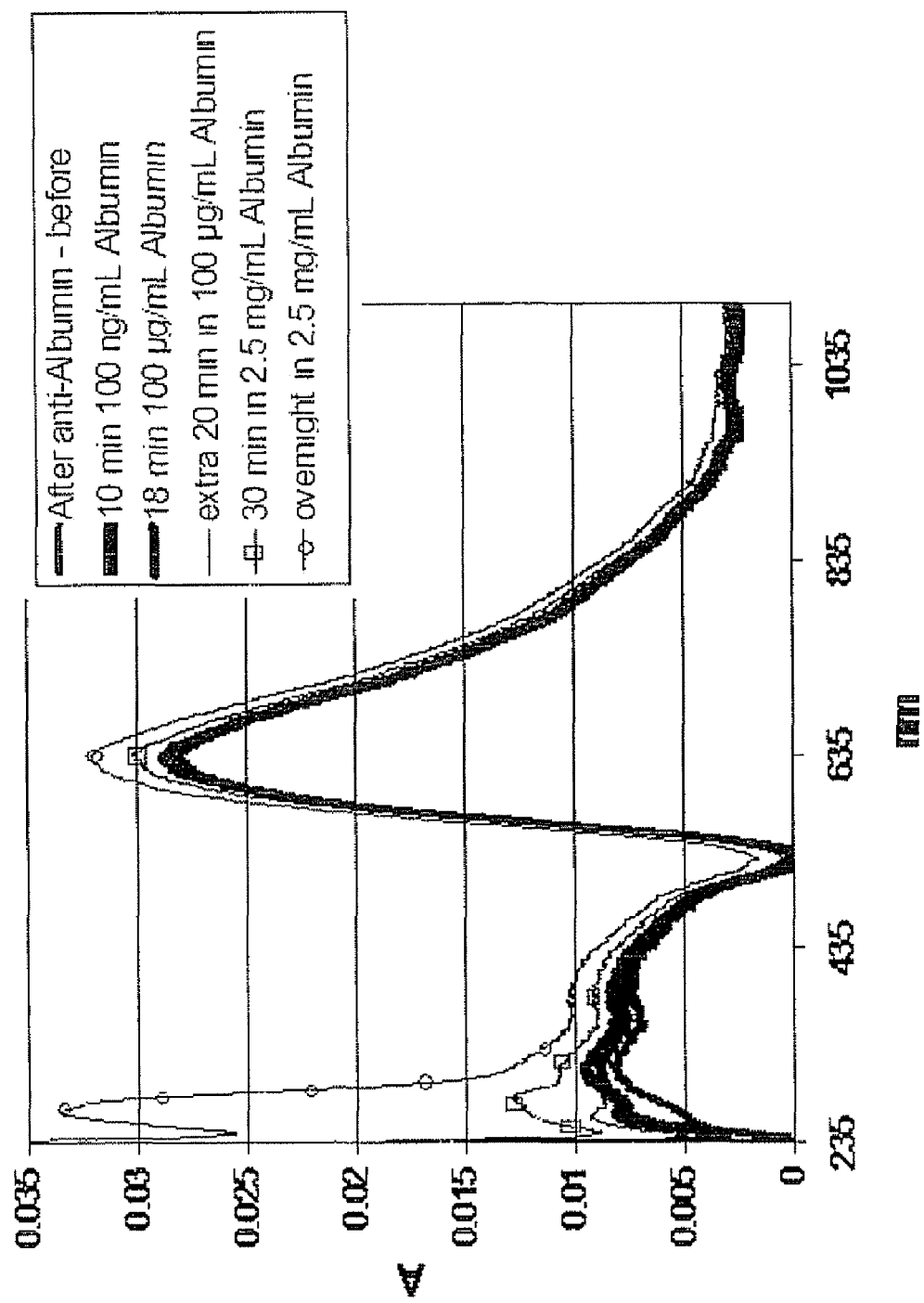
FIG. 6 is a graph illustrating difference spectra for various immunosensing applications in accordance with the invention.

FIG. 6 is a graph illustrating difference spectra for various immunosensing applications of an example method. Immunosensing experiments were performed on a thin layer of plated gold (8 minutes of plating time), and demonstrate the potential of this sensing method for biosensor applications. A self-assembled-monolayer of 16-MHA was formed on the thin gold film during a 25 min deposition period. The achieved carboxylic terminated SAM was activated via the EDC/NHS method with a mixture of 0.2 M/0.2 M EDC/NHS for 10 min. Consequently, the amino groups of the lysine amino acids of anti-HSA (500 µg/mL in 10 mM acetate buffer pH=5) were covalently coupled to the activated SAM surface. The non-reacted activated groups were blocked by rinsing for 7 min with 1 M ethanolamine and the non-covalently bonded antibodies were removed by rinsing for 2 min with 10 mM glycine (HCl buffer pH=2.2). In this way, a monolayer of anti-HSA on the surface can be observed. As can be seen in FIG. 6, an enhancement in the spectra around 270 nm is visible, as is a peak shift at 600 nm. This change in the spectra can be used to determine the concentration of anti-HSA, as has been previously described.

Nanoparticle Effects on Absorbance and Transmittance

In the case of nanoparticles, the absorption spectrum of metal nanoparticles is determined, at least in part, by (i) the particles' plasmon resonances, (ii) by bulk interband absorption. The first mechanism, plasmon resonances, is collective oscillations of the conduction electrons on the surface of the nanoparticles. In this respect, the resonance frequency of a particle plasmon is determined mainly by the dielectric properties of the metal and the surrounding medium, respectively, and by the particle shape, i.e., the ratio of the principle axes. Such resonances may result in narrow, spectrally-selective absorption and an enhancement of the local light field confined on, and close to the surface of the metal particle. Thus, the surrounding medium influences the plasmon frequency and the amplitude of the absorption.

The second mechanism that plays a role in light absorption by small metal particles, as noted above, is photon interband absorption. Photon interband absorption involves the promotion of an electron from the occupied d-level state in a metal to an empty state above the Fermi level. Therefore, the absorption is strongly determined by the joint density of d and s states of the conduction electrons. Strong absorption indicates a "parallel" energy dispersion function. In this regard, different peaks in the spectrum can be assigned to different interband absorption peaks. Due to the large skin-depth of a few microns, the nano-particles absorb light in the whole bulk area of the particle.

By increasing the dielectric constant near the nanoparticle surface, an increase of the density of the electromagnetic field at the particle's position enlarges the transition probability and, as such, the absorption for bulk transitions. This effect is only visible when the particle is smaller than the wavelength of the impinging radiation because such an object has too small a size to support any purely internal optical modes. The electric field operator internal to such a sphere is determined by the extended modes, hence the dielectric constant of the surroundings.

As the dielectric constant increases, an increase in absorption is expected, as has been experimentally verified. However, this relationship may be different for particle plasmons, as the dielectric constant of the surroundings also has a strong influence on the "wave number" and strength of the collective and evanescent mode of excitations. By coating the particles with a different material, both a shift in frequency and absorption probability is seen.

The change in dielectric constant is largest at the molecular resonance. The effect of molecular recognition between the analyte molecule and the receptor molecule is translated in a strongly enhanced bulk absorption signal at this resonance. Also the strength of the analyte molecular resonance will be altered by the presence of the particle after recognition event. Enhanced molecular absorption at resonance leads to a strong detection signal.

Compared to SPR measurements, the methods described herein have several advantages. For example, these methods are typically simpler to implement and associated apparatus can be manufactured at a relatively low cost as compared apparatus for use with SPR measurement. Moreover, the methods and apparatus described herein allow for differing configurations, which are easily integrated into different biological tools. As yet another advantage, a normal UV-Vis spectrometer may be used for the spectral measurements, which may also provide a cost savings. In still yet another advantage, the intensity of the incoming radiation doesn't have to be focused. Therefore, relatively inexpensive radiation sources may be used, which may provide still further cost savings as compared with prior art techniques. Of course, a laser (or other focused source) may be used as a radiation source, but is not necessary.

Figure 7:
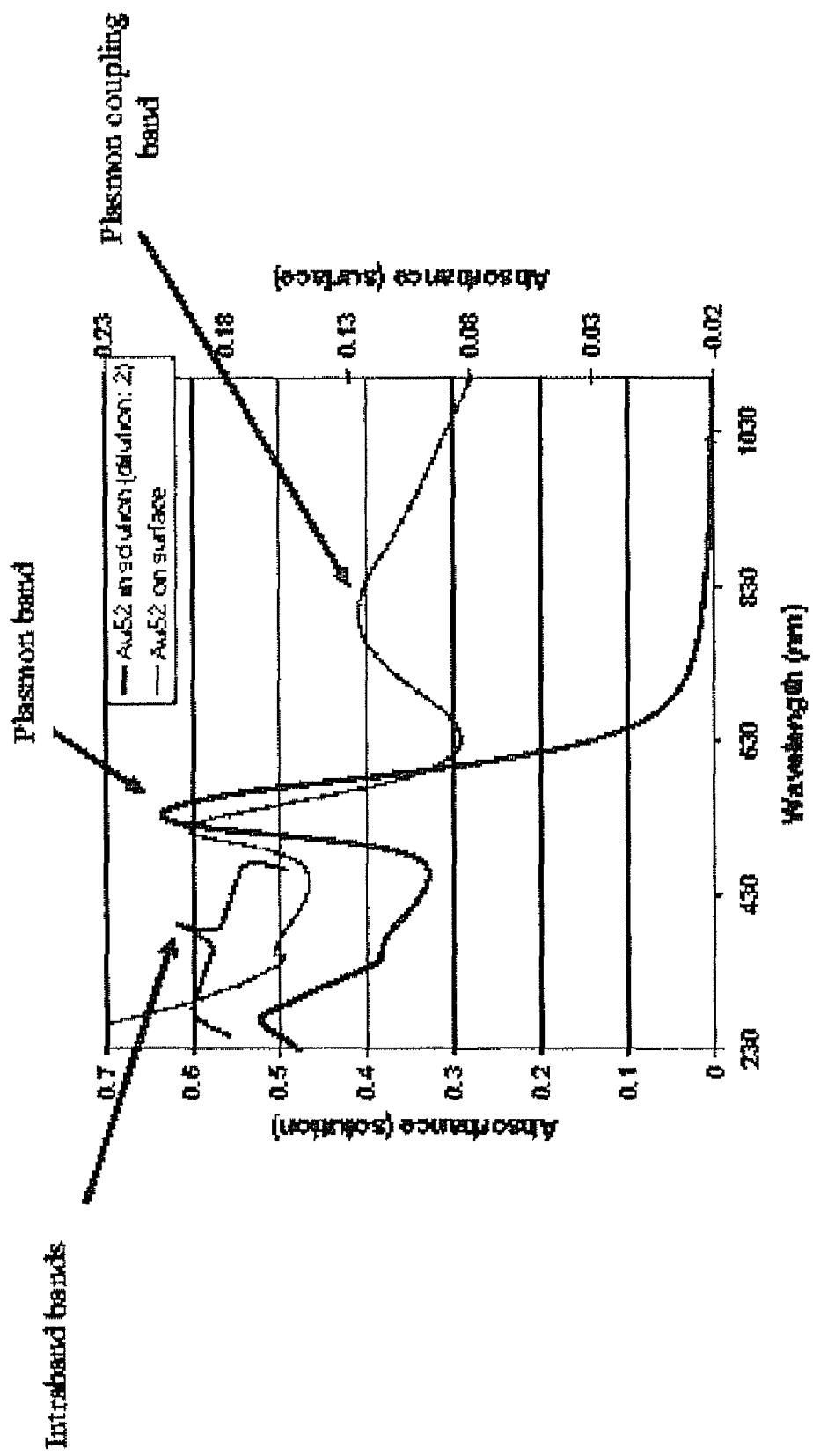
FIG. 7 is a graph illustrating absorbance spectra of Au particles in solution and on a surface.

FIG. 7 illustrates different absorption bands for a substrate in a sample solution where particles are both in solution and covalently immobilized on the substrate. The particles in solution and on the surface both show intraband absorption bands, as designated in FIG. 7, while particles on the substrate surface also show an additional plasmon coupling absorption band, as is also designated in FIG. 7. The different absorption bands display different characteristics, which are discussed below.

The plasmon absorption band is generally the most intense band of those studied. The origin and the position of this band can be explained by the dynamics of the conduction electrons in nanoparticle(s) of a substrate, such as described above. For particles much smaller than the wavelength(s) of the incident radiation, the electrons in the particles move in phase, e.g., the electrons may be considered to generate a dipole under the influence of the incident radiation. Electron motion leads to the generation of surface polarization changes on each side of the particle, which act as a restoring force in the conduction electrons leading to a resonance frequency in the absorption spectrum. The resultant sharp band is called a surface plasmon absorption band. For larger metal particles, the electrons become "dephased" and the restoring force becomes weaker. Consequentially, the electrons will be "freer" and the absorption band will broaden substantially.

In addition to particle plasmon resonances, interband absorption bands are also observed. These interband absorption bands are generally less intense than the plasmon absorption band and are situated at shorter wavelengths as compared to the main plasmon absorption band. This is due, in part, to the fact that plasmon absorption bands are the result of collective oscillations of the conduction electrons on the surface of the small (nano) particle. The resonance frequency of this particle plasmon is determined mainly by the dielectric functions of the metal, the surrounding medium and by the particle shape, e.g., the ratio of the principal axes. These resonances lead to a narrow spectrally selective absorption and to an enhancement of the local light (radiation) field confined on, and close to the surface of the metal particle. The surrounding medium influences both the plasmon frequency and the amplitude of the absorption.

The interband absorption on the other hand involves the promotion of an electron from an occupied d-level state in the noble metal to an empty state above the Fermi level. This absorption is strongly dependent on the joint density of d and s states of the conduction electrons and, therefore, occurs at shorter wavelengths. Due to a large skin-depth, nanoparticles absorb light in substantially the entire bulk area of such particles. By increasing the dielectric constant near the nanoparticle surface, for example, by biomolecular adsorption, an increase of the density of the electromagnetic field at the particles position (basically a Lorentz local field correction) increases the transition probability and, as such, the absorption for bulk transitions.

This effect is only visible when the subject particle is smaller than the wavelength of the impinging radiation because such an object has too small of a lateral extent to support a purely internal optical mode. The electric field operator internal to such a sphere is determined by the extended modes and, hence, by the dielectric constant of its surroundings. At molecular resonances, a strong enhancement of absorption is observed. As the dielectric constant increases, an increased absorption is expected and experimentally verified. This may be different for particle plasmons because the dielectric constant of their surroundings also has a strong influence on the wave-number and on the strength of the collective and evanescent modes of excitation. If the particles are coated with a different material, both a shift in frequency and in absorption should be observed.

Plasmon coupling bands are generally situated at longer wavelengths and are typically broader than the plasmon absorption bands. If the inter-particle distances are on the order of the nanoparticle sizes or smaller, the surface plasmons may interact due to dipole-dipole coupling and give rise to the plasmon coupling bands. These bands can shift the plasmon bands to longer wavelengths. In specific cases, longitudinal (L) and transverse (T) plasmon-polarization modes of gold nanoparticles on a substrate surface can exhibit an energy split between the L and T modes and give rise to the additional plasmon coupling band.

Particle Enhanced Fluorescence

While mutual interaction between a metal nanoparticle and an organic bio-molecule enhances absorption in the particle, the absorption of the analyte bio-molecule and related fluorescent and/or phosphorescent behavior is also influenced by the particle. For instance, a protein absorption line at a certain wavelength (e.g., about 280 nm) is related to the fluorescence of a free bio-organic molecule. This transition is dominated by symmetry considerations which are violated when in contact with a metal particle. Due to the disturbance of the wave functions and their symmetry, transitions in the molecule will be altered. Forbidden transitions will occur and an increase of absorption and fluorescence behavior will result. The size and form of the particle, and the distance between the particle and the molecule are thus important parameters that can be altered to obtain a desirable signal quality.

To take advantage of this situation, functionalized metal particles may be used to amplify the fluorescent behavior of a specific detector bio-molecule and, therefore, act as a sensing element. In our invention we use the increased absorption probability at about 280 nm (plus or minus 50 nm) of the bio-molecule next to the increased absorption at the same wavelength of the metal particle. Therefore, in the methods described herein, the radiation spectrum that relates to such absorption by the analyte-particle combination may be used to indicate the presence and/or concentration of an analyte.

Another implementation of the same detection principle can be achieved by measuring the fluorescent signal itself when particles are in a liquid or attached to a surface. By generating an affinity reaction, the fluorescence/phosphorescence of the bio-molecule in the analyte is amplified. The increased fluorescent or phosphorescent light intensity is a measure of the number of detection affinity events taking place in the liquid, or at the surface of the substrate. For such an approach, a wavelength selective scheme can be used to increase the signal to noise ratio. Because it is known that absorption and fluorescence/phosphorescence can happen at different wavelengths, the use of filters and excitation lines may be used to separate the incoming and outgoing signals, which may also result in an improved signal to noise ratio.

Coupled Transitions

In embodiments such as those described above, the plasmon or particle resonance has an influence on the 280 nm absorption line and the lifetime of the excited states in the particle or the molecule and vice versa. This influence allows one to make phase sensitive absorption and fluorescence measurements that may also be used to improve the signal to noise ratio. Such an approach includes exciting the molecule in a phase modulated fashion, such that the signal of the particle coming from the particle (plasmon) resonance will be modulated at the same frequency, allowing for a better signal to noise ratio and an increased sensitivity. In substantially similar fashion, phase modulated excitation of the particle resonance will influence the 280 nm absorption and, as such, allow for phase sensitive detection of this line.

Method for the Fabrication of a Substrate

Figure 8:
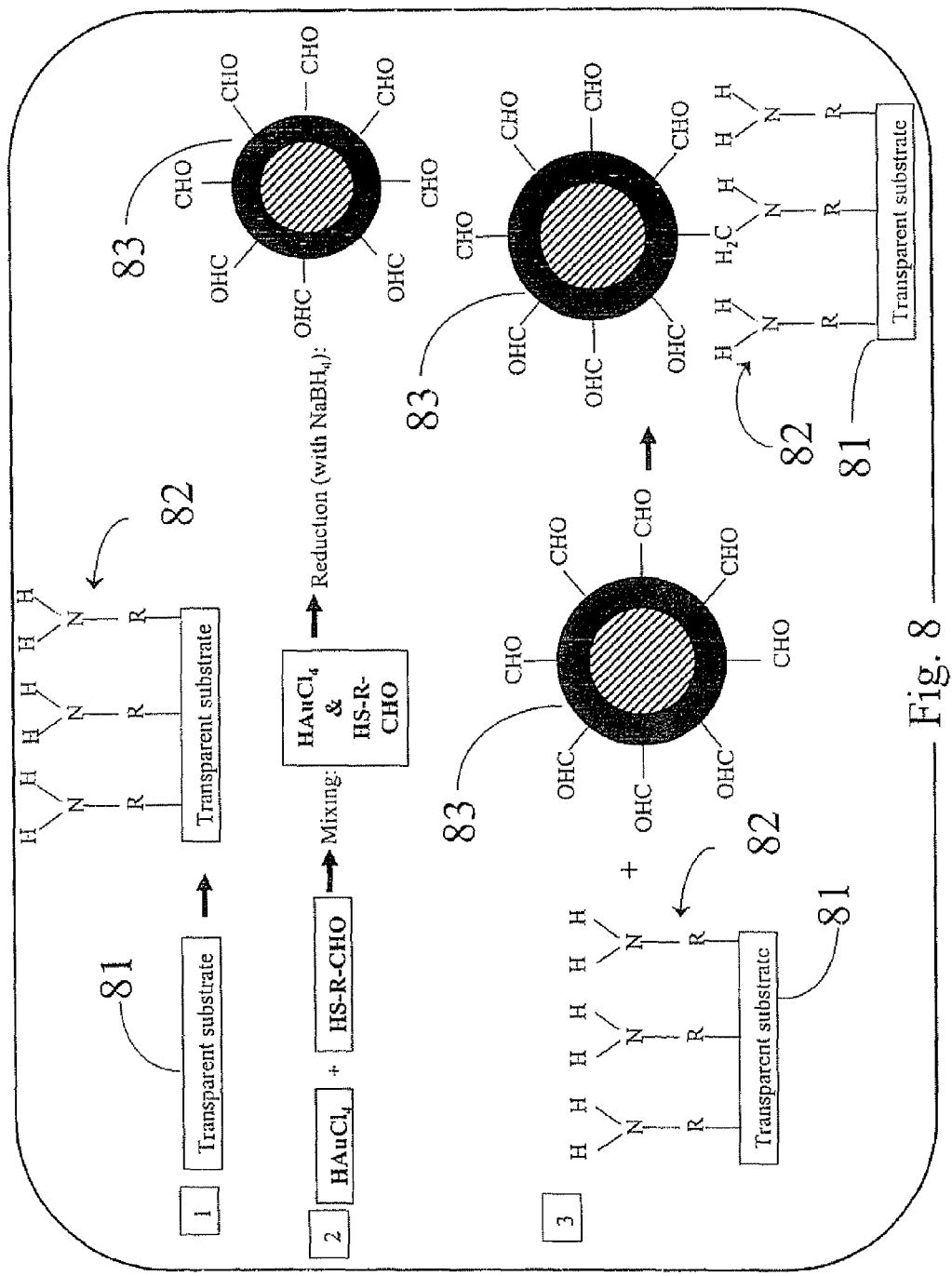
FIG. 8 is a drawing illustrating a schematic representation of a method for forming a conductive region and a recognition layer.

In one embodiment, a substrate comprising a conductive region and a recognition layer, as were described above, may be formed, for example, using the techniques illustrated in FIG. 8. Of course, other approaches are possible and the techniques shown in FIG. 8 are merely exemplary.

As is illustrated in section "1" of FIG. 8, a transparent substrate 81 is provided. As is also shown in section 1 of FIG. 8, an intermediate layer 82 is deposited on the substrate 81. Such an intermediate layer 82 (which may be formed as a self-assembled monolayer, for example) may be termed an "adhesion" layer or "linking" layer, as has been previously discussed.

In section "2" of FIG. 8, in-situ synthesis of (pre-activated) thiols on nanoparticles 83 is illustrated. The nanoparticles 83, in section "3" of FIG. 8, react (e.g., bind or adhere) with the intermediate layer 82 on the transparent substrate 81. The pre-activated thiols 83 may directly react with bioreceptors (an analyte) to bind the analyte for detection and/or determination of analyte concentration, as has been previously described. Alternatively, the pre-activated thiols 83 may react (e.g., adhere) directly with the substrate 81 without the use of the intermediate layer 82. Further, it will be appreciated, that in certain embodiments, the substrate 81 includes a conductive region, as has been previously described.

Alternative Substrate

Figure 9:
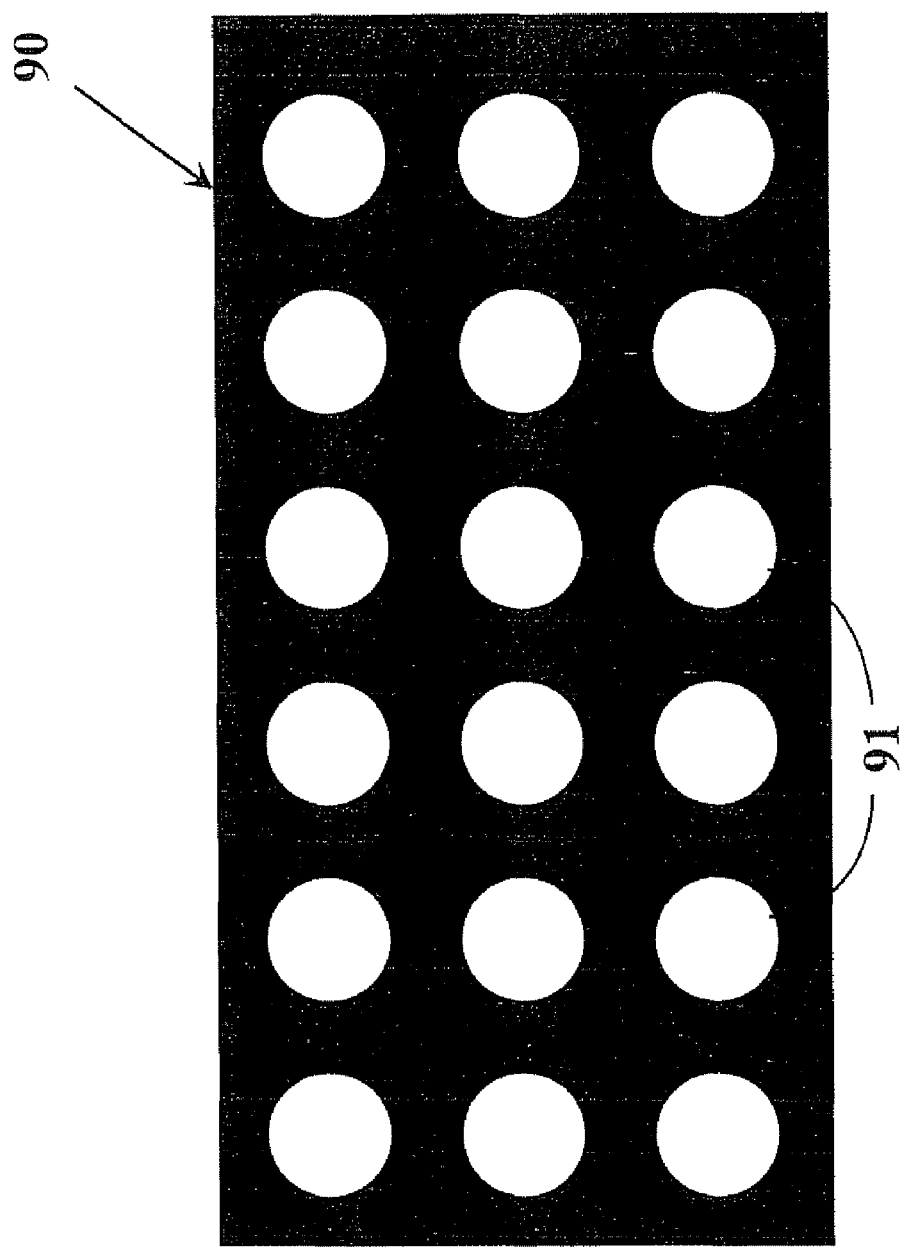
FIG. 9 is a drawing illustrating a top view of a nanoparticle film.

FIG. 9 illustrates an alternative substrate 90. The substrate 90 may be manufactured by forming a plurality of holes 91 in a continuous film. The holes 91 provide for making the substrate 90 transparent to radiation used for detection of an analyte and/or determining the concentration of the analyte, as described herein. The substrate 90 may also be viewed as particles that are in contact with each other while the spacing between the particles is constructed of circles, e.g., the holes 91.

Films used to form the substrate 90 take the form of materials that demonstrate predetermined absorption spectra. After binding functional self-assembled monolayers, bioreceptors and analyte with the substrate 90, the absorption spectrum is changed due to the change in the effective dielectric constant at the metallic interface as a result of molecular absorption. This allows for quantitative sensing of bioreceptor-analyte interactions. Films used for forming the substrate 90 may be semi-transparent films that are formed from various materials such as metals, semi-conductive materials and/or alloys.

The substrate 90 may be formed using any number of techniques. For example, the substrate 90 may be formed using classical photolithography techniques. Alternatively the substrate 90 may be formed using electron-beam techniques. Still alternatively, the substrate 90 may be formed using a polystyrene nanoparticle template method. A method of such an approach is illustrated in FIG. 10.

Figure 10:
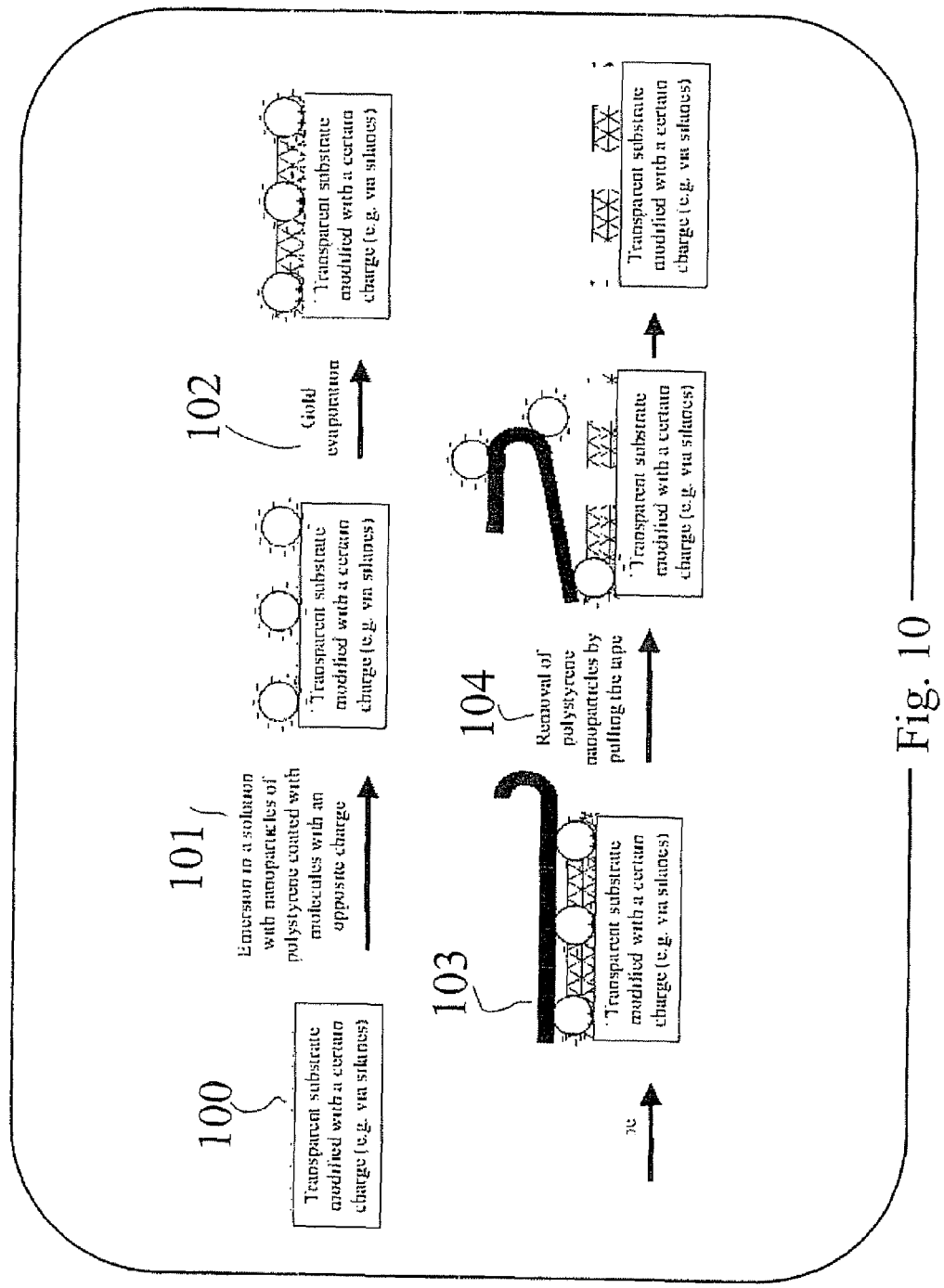
FIG. 10 is a drawing illustrating a schematic representation of a method for forming a substrate using a "polystyrene nanoparticle template" method.

The method of FIG. 10 includes providing a transparent substrate (as step 100), where the substrate is modified with a first charge. The substrate is then immersed (as step 101) in a solution that includes nanoparticles of polystyrene coated with molecules with a second charge, where the second charge is opposite to the first charge. The method illustrated in FIG. 10 further includes performing a gold evaporation operation (as step 102), and providing a device or apparatus for particle removal (as step 103). Such an apparatus may be, for example, an adhesive coated tape. The method illustrated in FIG. 10 further includes (as step 104) removal of the polystyrene nanoparticles using the device or apparatus provided in step 103.

In an alternative embodiment, a method for (i) preparing a substrate and (ii) for detection of (and/or determining the concentration of) an analyte in a sample may be implemented as follows. A transparent substrate that includes a conductive region is provided. The substrate has chemical molecules deposited on at least one of its surfaces. Such a substrate may be termed a "functionalized substrate". The chemical molecules may have two end groups. A first end group binds to the surface of the substrate, while the second end group binds to the nanoparticles of the conductive region.

The nanoparticles are covalently bound to the functionalized substrate. A nanoparticle film may be deposited via self-assembly from a nanoparticle containing solution, e.g., via evaporation, epitaxial growth and/or electroless plating. These nanoparticles may include chemical molecules with functional groups that can bind recognition molecules, such as, for example antibodies. Alternatively, surface nanoparticles can be modified with self-assembled monolayers that have functional groups that can bind recognition molecules.

The substrate may then be subjected to a reference buffer solution that is known not to contain any analyte. After exposure to the reference buffer solution, the substrate is subjected to radiation and the radiation that is absorbed by (or transmitted through) the substrate is measured. Once this reference measurement (reference spectrum) is made, the films (substrate) are subjected to the sample. If the specific analyte is present in the sample, the analyte (antigen) then binds to the antibody.

After exposure to the sample, the substrate (e.g., while in the reference buffer solution) is again exposed to the radiation source that was used to determine the reference spectrum.

The radiation absorbed or transmitted is again measured to determine a sample spectrum. The difference between the reference spectrum and the sample spectrum (e.g., in the UV, VIS and near-IR region thus intraband, plasmon and plasmon coupling absorption bands) provides both qualitative and quantitative information on the concentration of the analyte in the sample.

Such a differential measurement may be performed by measuring the difference between two substrates where a first substrate is coated with a molecule for nonspecific binding of the analyte, while the second substrate is coated with recognition molecule(s) for specific binding with the analyte (e.g., an associated antigen) of interest. In this approach, there is no need for a reference buffer solution.

Sandwich Assay

Figure 11:
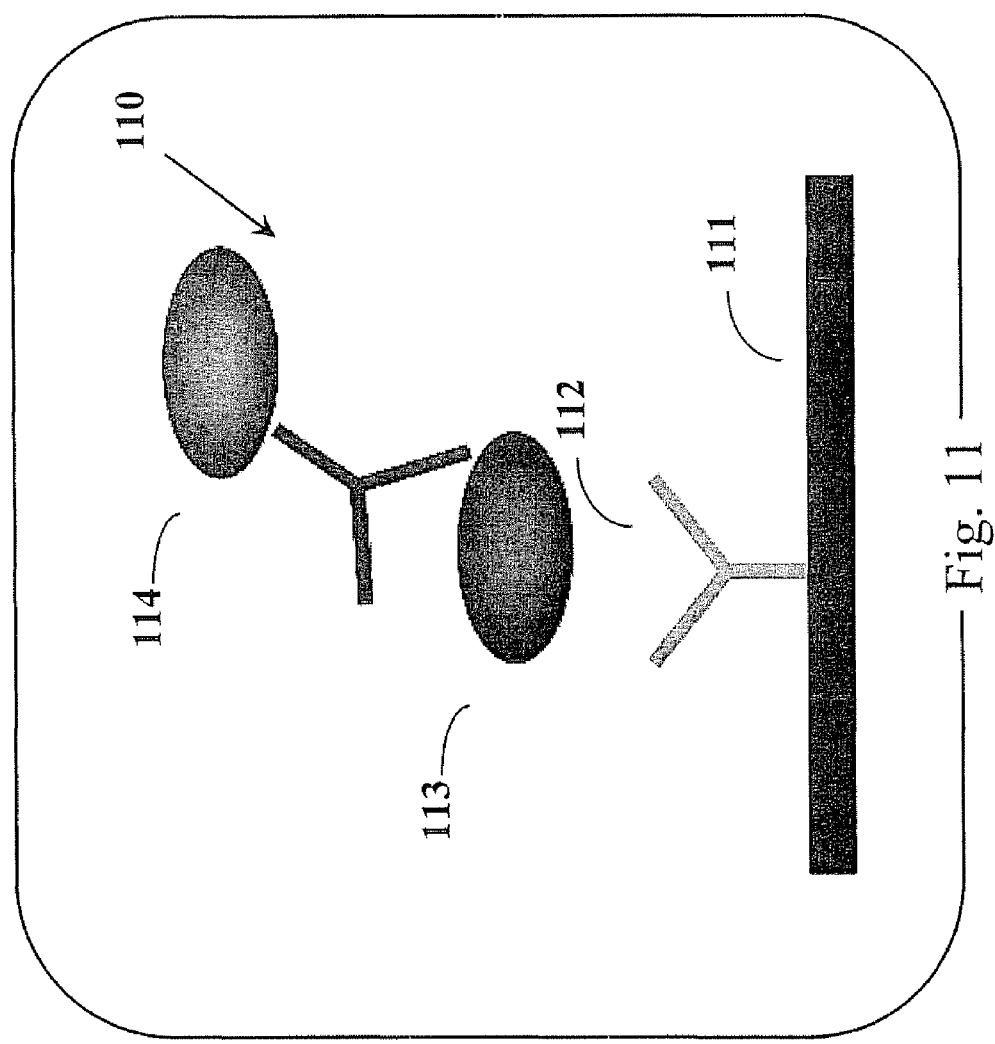
FIG. 11 is drawing illustrating a schematic representation of a sandwich assay.

As yet another alternative, a sandwich assay may be used with the methods described herein. Such a sandwich assay 110 is illustrated schematically in FIG. 11. The sandwich assay 110 includes a substrate 111 that includes a conductive region and a recognition layer. The recognition layer includes a recognition molecule 112 that can bind an analyte 113 with a secondary antibody 114. The secondary antibody 114 may contain a metal, a semiconductor material and/or an alloy. In such approaches, nanoparticles may also be used. This approach may further modify the absorption characteristics and could, therefore, enhance the sensitivity of detection and/or concentration determination.

Competitive Assays

Figure 12:
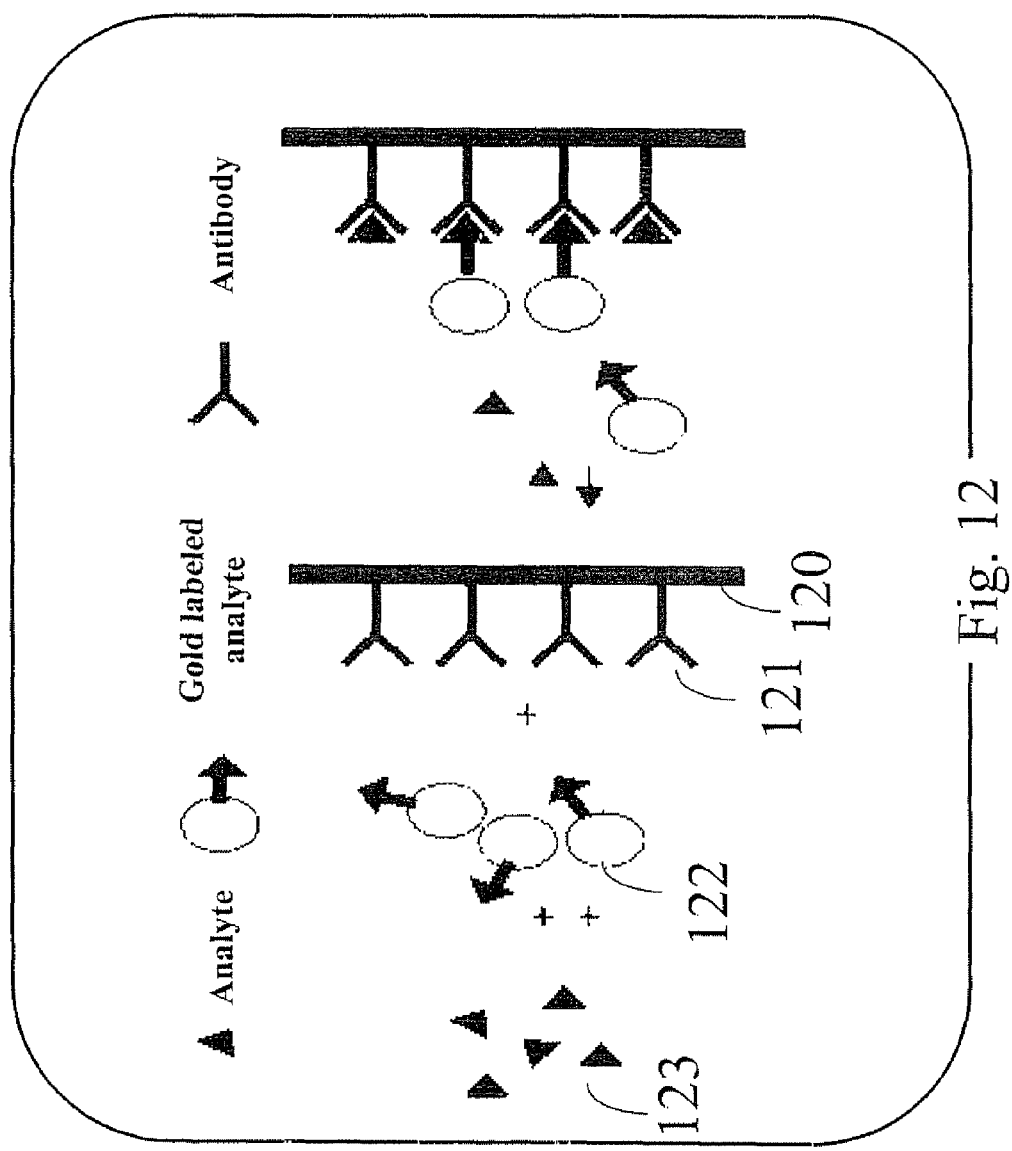
FIG. 12 is a drawing illustrating a schematic representation of a competition assay.
Figure 25:
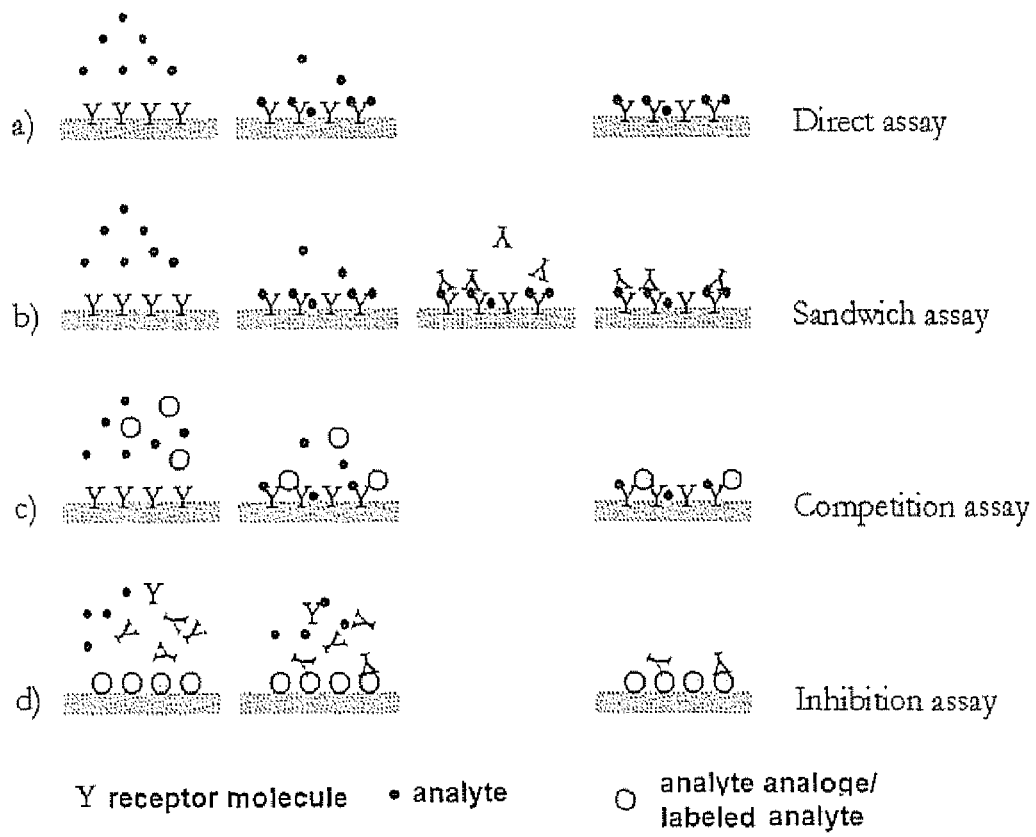
FIG. 25: Schematic presentation of the different immunoassay formats that can be used a) the direct assay, b) the sandwich assay, c) the indirect competition assay and d) the indirect inhibition assay.

In other example embodiments, competitive assays with antibodies or competitive agents containing metal, semi-conductors, alloys or other materials may be used to determine the presence and/or concentration of an analyte. One example of the use of such an indirect competitive assay, the so called "competition assay", is illustrated in FIGS. 12 and 25. As is shown in FIG. 12, a recognition molecule 121, such as an antibody, is deposited onto a conductive region of a substrate 120. Next, a sample is prepared, where the sample includes a gold-labeled analyte 122 at a known concentration and a non-labeled analyte 123 at an unknown concentration. The substrate 120 (with the recognition molecule(s) 121) is subjected to the sample, where binding with the gold-labeled analyte 122 and the non-labeled analyte 123 occurs. Using a competitive curve, the concentration of the unknown analyte may be determined based an analysis of the substrate 120 using previously described techniques.

Optical Fiber Apparatus

Figure 13:
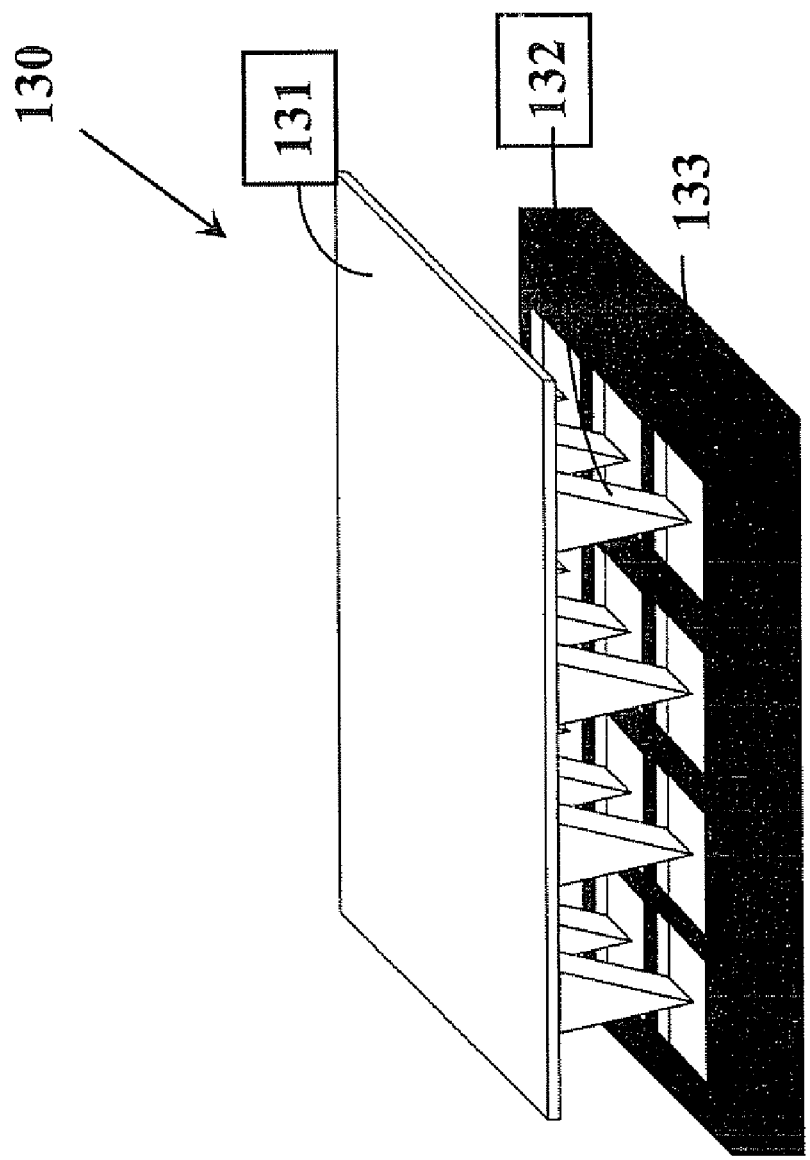
FIG. 13 is a drawing illustrating a sandwich assay apparatus.

Another apparatus 130 that may used to implement methods for detecting and/or determining the concentration of an analyte (or analytes) is illustrated in FIG. 13. The apparatus 130 includes a fiber substrate 131. Such substrates may have at least one optical fiber coupled with a surface of the substrate. The apparatus 130 shown in FIG. 13 includes an array of optical fibers 132 coupled with a surface of the substrate 131.

The optical fibers 132 may be coated with a "conductive region". The conductive region may be implemented in like fashion as has been described above. The conductive region is also operatively associated with a biological recognition layer, as has been previously discussed. For example, the recognition layer may be constructed of a self-assembled monolayer with immobilized antibodies. Alternatively, DNA strengths, enzymes, ion-selective molecules, or any number of other immobilized receptor molecules may be used.

For the apparatus 130, the array of optical fibers 132 coupled with the surface of the substrate 131 is compatible with a microtitre plate 133. The microtitre plate 133 may be a standard microtitre plate. Further for the apparatus 130, each optical fiber 132 may be coated with the same or different conductive region material. Likewise, the conductive region of each optical fiber 132 may be operatively associated with the same, or with different recognition layer molecules.

In such an approach, each well of the microtitre plate 133 may contain the same sample, or may contain different samples. By placing different samples in each of the wells of the microtitre plate 133, the apparatus 130 may be used for multiplex analysis of the different samples (or may be used for multiplex analysis of the same sample in each well using the same or different recognition molecules). In such multiplex analysis approaches, the analysis may be further varied by each optical fiber 132 containing a different recognition layer (e.g., different bioreceptors) and each well of the microtitre plate containing a different sample. It will be appreciated that any number of combinations of samples and/or recognition molecules may be used.

For the apparatus 130, the optical fibers 132 may be renewed after a recognition operation. For instance, the optical fibers are renewed by destroying the receptor-analyte binding. This destruction of bindings may be achieved, for example, by washing the substrate 131 in an appropriate regeneration solution. The apparatus 130 may then be used to perform another assay (recognition operation).

The apparatus 130 may also be used in conjunction with a method that includes modifying the optical fibers 132 with chemical molecules (such as Si or S-based self-assembling monolayers). The chemical molecules are selected such that they bind the "conductive region" material. For embodiments using SAMs, such SAMs may have functional groups such as mercapto, amino, $CH_3$, and the like.

The optical fibers 132 may then be dipped in one or more nanoparticle solutions to allow adsorption of the "conductive regions" onto the fibers. The nanoparticle films that are formed on the optical fibers 132 may also be produced by evaporation. The evaporated material may be metallic, semiconductive and/or an alloy, as has been previously discussed. For this embodiment, the nanoparticle films are then modified with Si-based self-assembled monolayers comprising functional groups. These functional groups can bind the recognition molecules (e.g. antibodies).

The method then includes performing a reference absorption measurement (in a reference buffer solution) by measuring light at the bottom of the microtitre plate 133 with the optical fiber 132 at the top in a well of the microtitre plate 133. Subsequently, the optical fiber 132 (or fibers) is (are) dipped in a well containing the sample/analyte. After exposure to the sample, the optical fibers 132 are then dipped in the reference buffer solution again. The change in absorption intensity/position before and after sample/analyte binding enables the determination of qualitative and quantitative information regarding the target analyte in the sample. The optical fiber 132 may then be renewed by exposing the optical fiber 132 to an appropriate regeneration solution.

Spectrum Changes

The apparatus and methods as described in this disclosure can be used to determine the presence and/or concentration of an analyte in a sample in any number of ways. First, the absorption/transmission difference of light through at least one substrate ("conductive region"+self-assembled monolayer+recognition molecule) is measured and used to allow for quantification of a specific analyte in a sample. Next, at least one sensor is subjected to the sample. Binding of a substance (the analyte) in the sample may result in a change of absorption/transmission of light by/through the substrate in a number of ways.

First, the wavelength attributed to a plasmon effect may shift. For instance, a plasmon peak is typically situated in the Vis and near-IR region. Both an absorption wavelength increase, as well as a change in an absorption peak position can be used for sensing.

Second, a wavelength at which intraband absorption occurs may be amplified by the analyte molecular resonance line. An intraband absorption peak is typically situated in the UV or Vis region. Both an absorption increase as well as a change in a peak position can be used for sensing.

Third, a wavelength associated with plasmon coupling may be used for sensing. In this situation, particles on the surface of a recognition layer may demonstrate other absorption characteristics than particles in solution. For example, some particles on the surface may show a secondary peak, which may be due to plasmon coupling, as is shown in FIG. 7. This absorption peak is typically situated in the Vis to near-IR to IR region and is normally situated at longer wavelengths than the plasmon peak. This absorption peak can be used for sensing bioreceptor-analyte interactions. Both the absorption increase and a change in the peak position can be used for sensing.

As an alternative to using individual spectrum characteristics, the UV-VIS-near IR-IR spectrum as a whole may be used as a "fingerprint" for sensing analyte specific interactions. It will be appreciated that any combination of these techniques and characteristics, as well as other similar techniques and characteristics may be used for analyzing analyte specific interactions.

Distance Between the Recognition Molecule and the Conductive Region

When the substrate is subjected to a sample containing the analyte, an interaction occurs (if the analyte is present) between the analyte and the recognition molecule (being part of the recognition layer). After such an interaction, radiation is directed through the substrate. The transmission of radiation through the conductive region (such as a nanoparticle or discontinuous film) induces a localized surface plasmon resonance wave (resulting in the effects as described above) at the surface of the nanoparticles. However, the length of this surface plasmon resonance wave decays exponentially away of the conductive region. The extension of the localized surface plasmon resonance wave depends further on the nanoparticle properties (e.g., size and material). The surface plasmon resonance wave extends a maximum 80 nm and often less than 60 nm or 50 nm.

Figure 14:
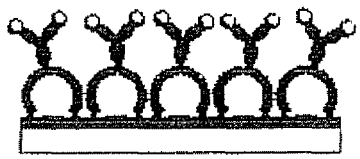
FIG. 14: Schematic drawing of an antibody-antigen interaction on a nanoparticle film, covered with self-assembled monolayers of thiols, which bind antibodies, which can bind antigen.

It is therefore very important that the binding event (interaction between the analyte and the recognition molecule) under investigation happens at a distance less than 60 nm from the nanoparticle surface, so closer than 60 nm from the nanoparticle surface, or even more preferably closer than 50 nm from the nanoparticle surface. This means that the distance between the conductive layer and the place of the molecule where the binding takes place is less than 60 nm or even better less than 50 nm. In case the substrate is a conducting substrate, the distance between this surface and the active region of the recognition molecules in the recognition layer is less than 60 nm or more preferably less than 50 nm. In addition, sensing closer to the conductive region gives rise to more sensitive measurements because the localized surface plasmon resonance wave and thus the sensitivity is decaying exponentially away from the surface. The setup of a typical experiment for detecting antibody/antigen interactions is represented in FIG. 14.

The sensing step of main interest (namely the antibody-antigen interaction or other affinity interactions) happens at a certain distance away from the surface of the nanoparticle film. Typical values of the different lengths important in this setup are:

Self-assembled monolayer of thiols or disulfide molecules: ~2 nm
This can be combined with binding to
Conventional antibody: ~15 nm
F(ab')$_2$ ~3-8 nm
Fab' ~3-5 nm
ScFv ~2-5 nm3
VHH ~2-5 nm The antibody-antigen interaction of interest occurs at least 17 nm away from the surface of the nanoparticle film. The sensitivity of the method of the present invention is increased by applying smaller bioreceptors as recognition molecule. This invention allows biosensing in a more sensitive way. Smaller biomolecules can be obtained in several ways.

Figure 15:
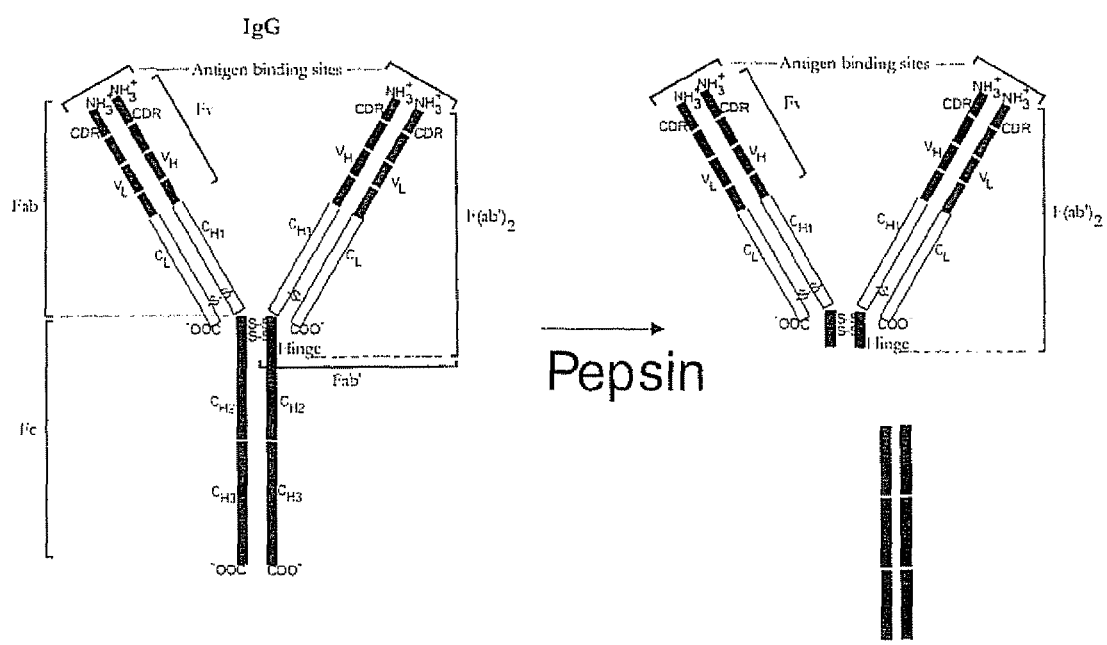
FIG. 15: Enzymatic cutting of an antibody to F(ab')$_2$ using pepsin.
Figure 16:
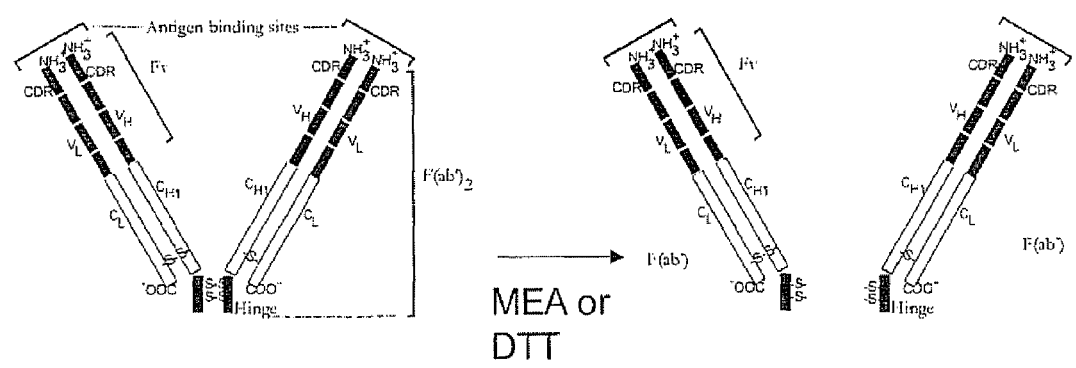
FIG. 16: Chemical reduction of a F(ab')$_2$ fragment to two fully active Fab' fragments.

In a first embodiment, conventional antibodies (of mouse, rat, goat, sheep), are cut into pieces. This step consists of different substeps. First, one subjects the antibodies to proteases (e.g., pepsine). The Fc part of the antibody will be removed (FIG. 15). This Fc part is not necessary to bind the antigen. An F(ab')$_2$ fragment (~3-8 nm) will be generated which presents two binding sites to bind the antigen. This is a smaller, fully active, fragment (Molecular Weight of ~110, 000 dalton) compared to the full length antibody (Molecular Weight of ~150,000 dalton). This F(ab')$_2$ fragment can further be chemically reduced via different chemical reduction agents, e.g., 2-mercaptoethylamine (2-MEA) (FIG. 16). This subsequent modification generates small Fab' fragments (~3-5 nm) with a molecular weight of ~55 000 Dalton.

Via the use of other enzymes and other reducing agents, F(ab)$_2$ fragments and Fab fragments can be generated. These fragments require a different coupling strategy to the self-assembled monolayers but the sensing efficiency will be similar. Applying these smaller fragments in combination with the method as described in the present invention can drastically increase the sensitivity of this invention.

In a second embodiment, single chain Fv fragments (ScFv) (2-5 nm) are generated. These fragments are produced via recombinant techniques starting from conventional full length antibodies. Details of the production, advantages, and disadvantages are known by those of ordinary skill in the art. These single chain Fv fragments are also fully active fragments which can bind the antigen. In addition, they are even smaller in size. These fragments have typically a molecular weight of 25 000 Dalton.

Figure 17:
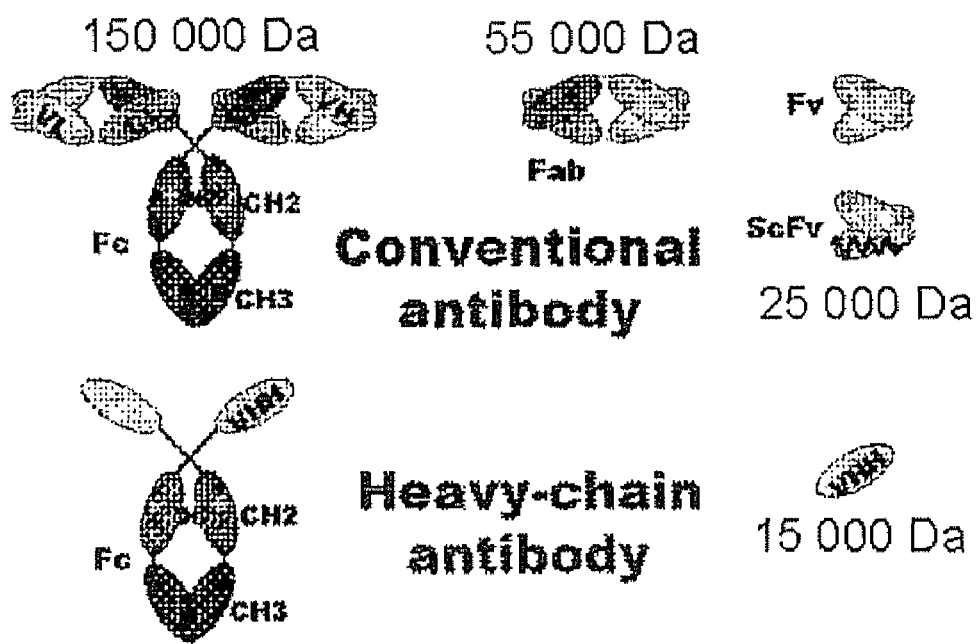
FIG. 17 Top: Conventional antibody structure and its fragments (Fab, Fv, ScFv). Bottom: Heavy Chain antibody and its VHH fragment

In a third embodiment, recombinant camel antibody fragments are generated and applied in combination with the current invention. These fragments are produced via recombinant techniques starting from 'heavy chain antibodies', which are presented in a limited number of different families of animals. Details of the production, advantages, and disadvantages are known by those of ordinary skill in the art. These VHH fragments are also fully active fragments which can bind the antigen and are even smaller in size. They have typically a molecular weight of 15 000 Dalton (2-5 nm) and are therefore the smallest fully active fragments that can bind antigens (FIG. 17). These fragments are therefore ideal to perform sensitive biosensing experiments with the technology described in this invention.

Figure 22:
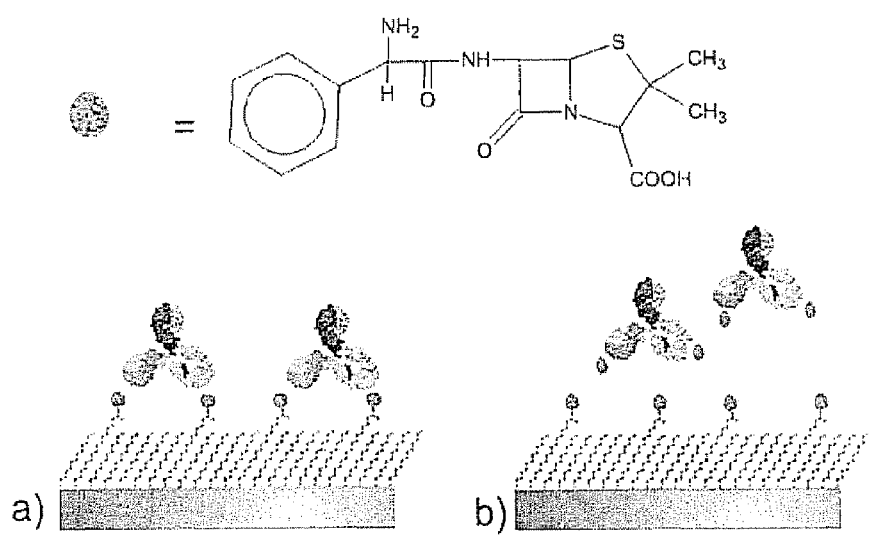
FIG. 22: (a) penicillin specific antibodies are bound to the surface modified with the analyte analogue (ampicillin). (b) the surface bound antibodies are replaced by the analyte molecules (ampicillin) in the sample.

In a fourth embodiment, a small molecule (hormone, peptide, antibiotic, etc.), typically smaller then 3 nm, or even below 1 nm is bound on the nanoparticle surface (FIG. 22). This approach is often used in indirect competitive assay formats such as an inhibition assay (FIG. 25). This latter is often used for the detection of low molecular weight compounds (LMW) such as hormones, antibiotics, pesticides, etc. In such an inhibition assay for LMW compounds an analyte analogue is immobilized on the sensor and the free analyte (in solution) competes with the analyte analogue immobilized on the sensor surface for binding sites on the antibody in solution. In this type of assay, the transducer can differentiate the relative amount of antibody binding sites occupied by the analyte in the sample. This results in a sensor signal that is inversely proportional to the analyte concentration.

In a typical inhibition experiment, one first has to determine the maximum antibody loading onto the surface. Subsequently the same amount of the antibody is mixed with the analyte and flowed over the surface. The inhibited binding of the antibody with the analyte in solution and on the surface is a measure of the concentration of the sample after determination of the maximum binding signal in the first step.

A variant on the inhibition assay is the replacement assay. In a replacement assay an antibody or antibody fragment is bound to this surface-immobilized analyte analogue. Next, this antibody-modified surface is subjected to the sample containing the analyte. The analyte in the sample will go into competition with the antibodies bound onto the surface and a decrease of the signal will be observed which can quantitatively be interpreted.

The advantage of these approaches on the TPB technology compared to normal antibody-antigen assays relies again on the distance of the binding event and the nanoparticle substrate. As mentioned before, the electromagnetic field strength of the nanoparticles decays with the distance from the surface and is dependent on the size of the particles (Zeman et al., 1987). This implies that the sensitivity will decrease with the distance from the surface of the particles. Studies with 15 nm particles showed that the penetration depth of the electromagnetic field extends 20-50 nm from the nanoparticle surface (Okamoto et al., 2000), while Nath et al. (2004) could demonstrate that particles of 39 nm could detect refractive index changes at distances greater than 40 nm. For assay formats with a thiol layer (2-3 nm) and an antibody (~15 nm) immobilized on the particles, the binding event will happen at ~18 nm distance from the surface. In the inhibition assay and replacement assay no antibody but a LMW compound (ampicillin) is immobilized onto the gold nanoparticles, the binding event will thus take place closer to the surface (4-5 nm) which overcomes the drawback of decaying sensitivity away from the surface.

Experiment

Figure 18:
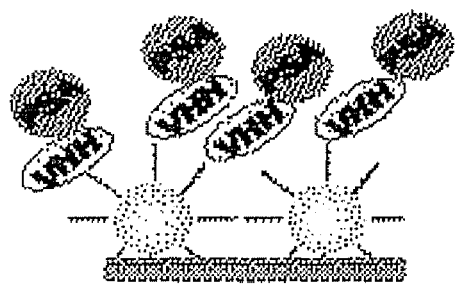
FIG. 18: Schematic representation of the performed experiment concerning PSA detection using VHH fragments

This experiment shows how VHH fragments of camel antibodies can give rise to an enhanced sensing performance. The schematic setup of the experiment is shown in FIG. 18. Quartz slides were first cleaned for 10 min with a piranha solution (1/3 $H_2O_2/H_2SO_4$), rinsed with water and functionalized with 3-mercaptopropyltrimethoxysilane (10% in 95/5 ethanol/water) for 3 h. Next, the samples were rinsed with ethanol and dried in an oven for 10 min at 108° C.

A film with 50 nm gold nanoparticles was produced by self-assembly from a nanoparticle containing solution. The gold nanoparticles (50 nm) were produced via the procedure described by Frens (Frens, G. *Nat. Phys. Sci.* 1973, 241, 20). The concentration of gold nanoparticles was increased 10 times by centrifugation at 5000 g for more than 30 minutes. The nanoparticles were bound on the mercapto-silane functionalized quartz slides by incubation overnight. This enabled a covalent binding between the thiol-groups on the functionalized quartz slides and the gold surface of the gold nanoparticles. Afterwards, the slides were rinsed with DI water and dried under a stream of nitrogen gas.

Figure 26:
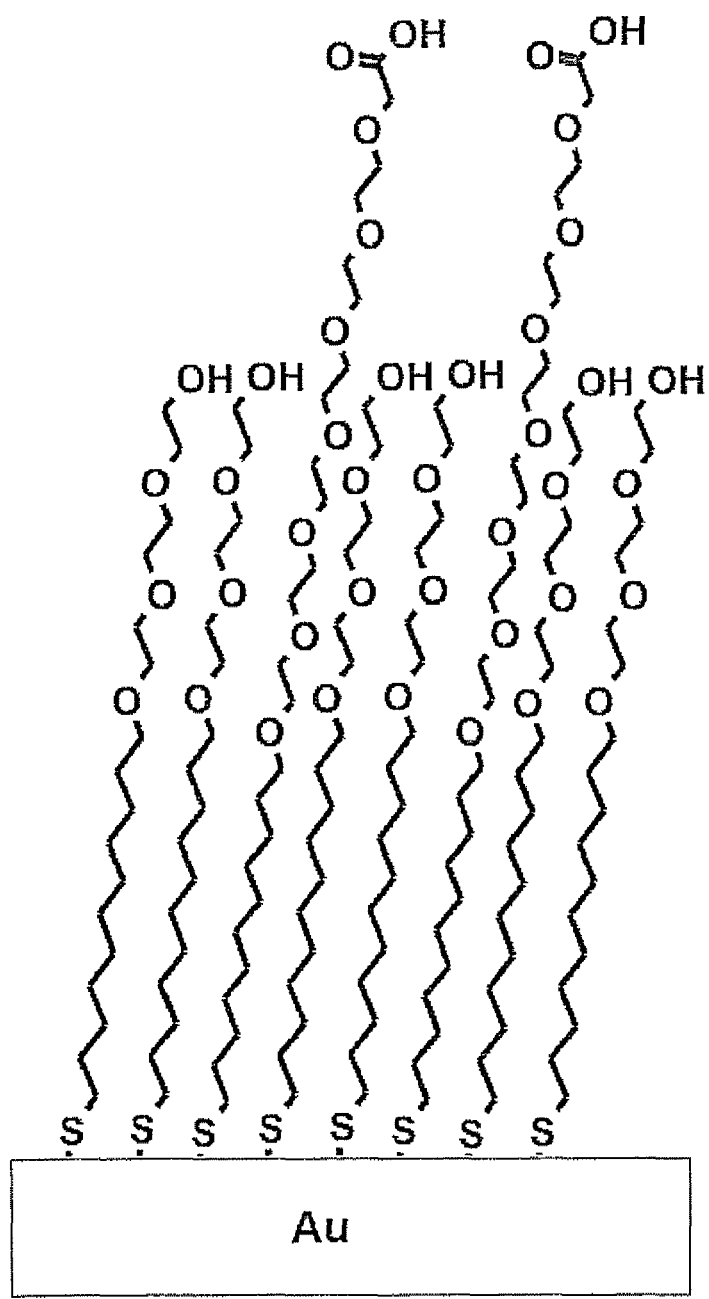
FIG. 26: Mixed self-assembled monolayer to functionalize the surface of the gold nanoparticles.
Figure 27:
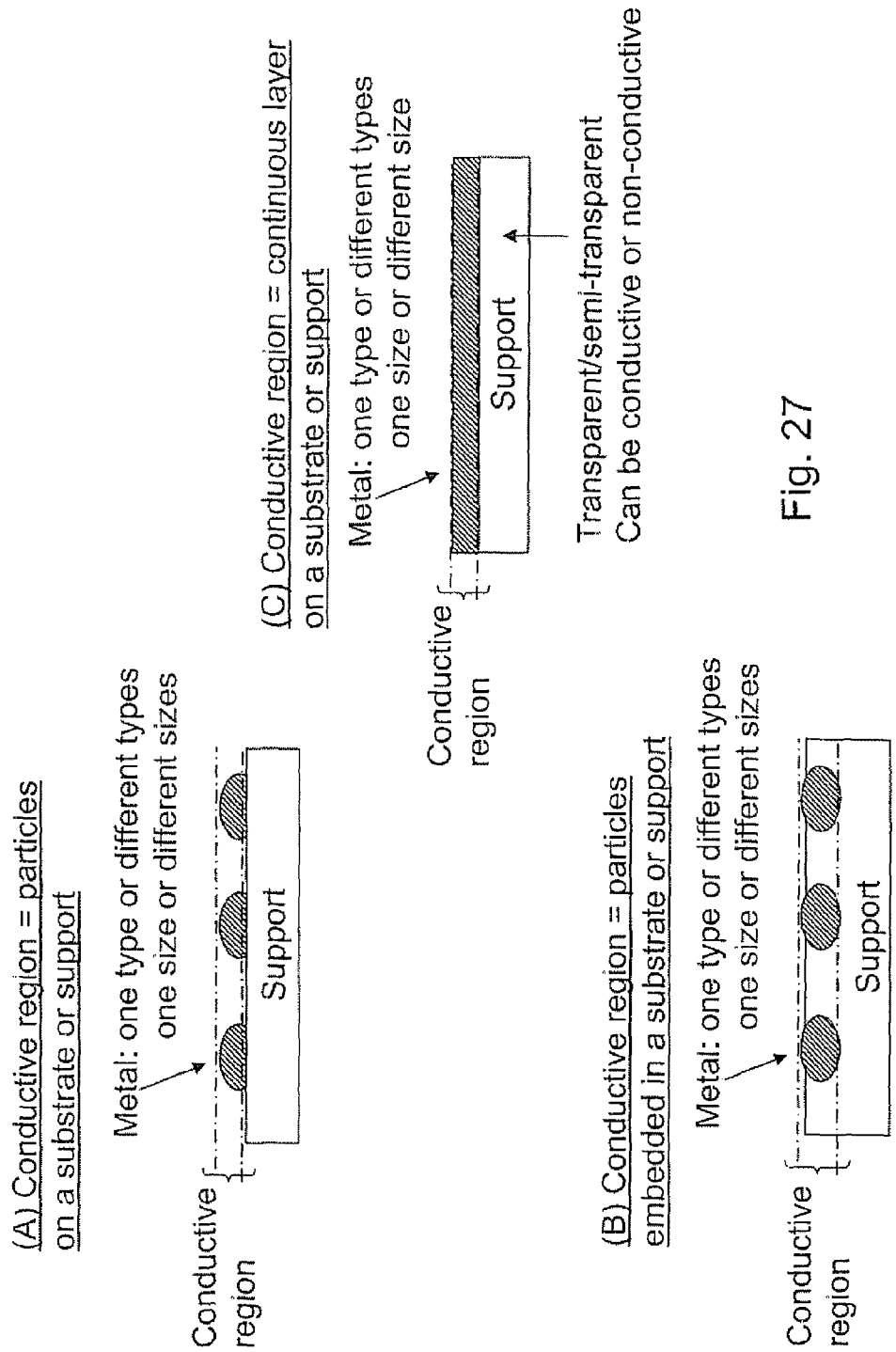
FIGS. 27(A)-(E): Schematic representations of various configurations of the conductive region.

Subsequently, self-assembled monolayers of thiols were deposited onto this nanoparticle film. The slides were functionalized with thiol molecules to allow the covalent binding of the different bioreceptors or bioreceptor fragments. Therefore, the slides were immersed in 5/95 (v/v) 2-(2-(2-(2-(2-(11-mercaptoundecyloxy)ethoxy)ethoxy)ethoxy) ethoxy)-ethoxy)ethoxyacetic acid and 2-(2-(2-(11-mercaptoundecyloxy)ethoxy)ethoxy) ethanol in ethanol for 1 hour. The resulting surface consisted of a gold nanoparticle surface functionalized with both carboxylic groups to allow the coupling with the bioreceptors or bioreceptor fragments and poly(ethylene-oxide) groups to avoid non-specific adsorption (N. Geukens, F. Frederix, G. Reekmans, E. Lammertyn, L. van Mellaert, W. Dehaen, G. Maes, J. Anné, 'In vitro analysis of type I signal peptidase affinity and specificity for preprotein substrates by surface plasmon resonance', *Biochemical and Biophysical Research Communications* 2004, 314, 459). This is illustrated in FIG. 26.

Bioreceptors were coupled using EDC/NHS method (F. Frederix, K. Bonroy, W. Laureyn, G. Reekmans, A. Campitelli, W. Dehaen and G. Maes, 'Enhanced performance of a biological recognition layer based on mixed self-assembled monolayers of thiols on gold', *Langmuir* 2003, 19(10), 4351). Both camel antibody fragments as conventional monoclonal mouse antibodies were applied. The specifications of both types of bioreceptors are described in D. Saerens et al (D. Saerens, F. Frederix, G. Reekmans, K. Conrath, K. Jans, L. Brys, L. Huang, E. Bosmans, G. Maes, G. Borghs, S. Muyldermans, 'Engineering camel single-domain antibodies and interphasechemistry for human prostate-specific antigen biosensing', *Analytical Chemistry* 2005, 77(23), 7547) and Huang et al (L. Huang, D. Saerens, G. Reekmans, J.-M. Friedt, F. Frederix, L. Francis, S. Muyldermans, A. Campitelli, 'The Combination of mixed Self-Assembled Monolayers and VHH camel antibodies for Enhanced PSA Immunosensing', *Biosensors and Bioelectronics* 2005, 21, 483).

Figure 19:
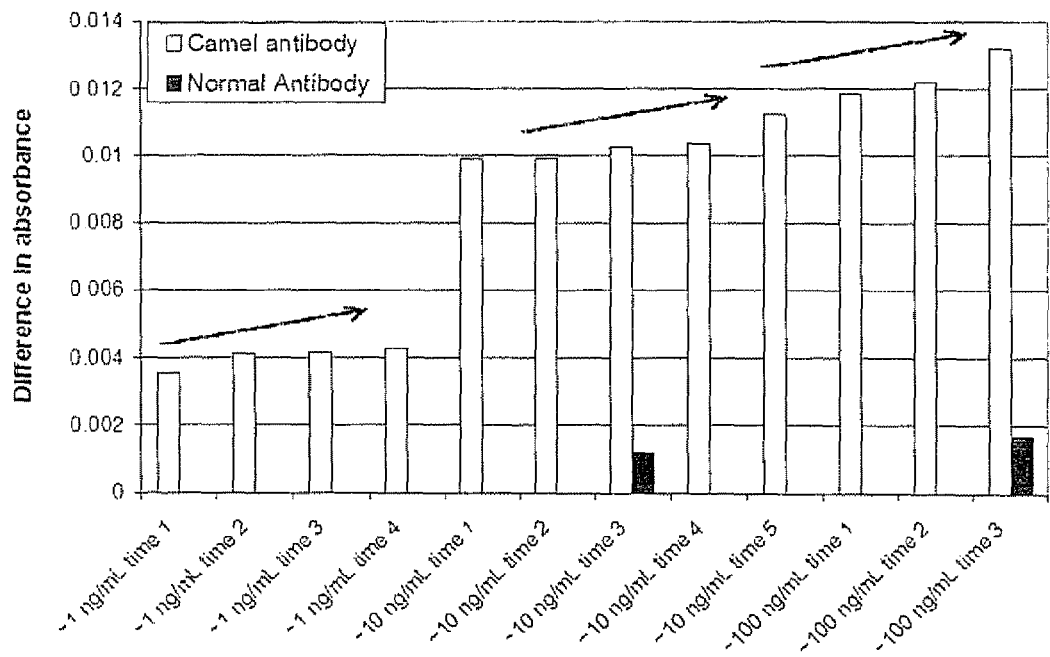
FIG. 19: The detection of different concentrations of PSA measured after different time frames using the differential transmission plasmon biosensing measurements. The white bars indicate the results using camel antibody fragments as bioreceptors, while the black bars indicate some results realized using normal mouse monoclonal antibodies.

The actual localized surface plasmon resonance or transmission plasmon biosensor experiments were performed using differential measurements with a Shimadzu UV-1601PC spectrophotometer with a slit width of 2 nm and a data interval of 0.5 nm. The aim is to detect the prostate specific antigen (PSA, SCIPAC) at different concentration in HBS (10 mM 4-(2-hydroxyethyl)piperazine-1-ethanesulfonic acid, 150 mM NaCl, 3.4 mM ethylenediaminetetraacetate, and 0.005% Tween 20 (pH 7.4)). Differential measurements implies that the difference UV-Vis absorption spectrum is measured between an antibody coated functionalized quartz slide and slide without an antibody upon contact with the PSA containing sample. Differential measurements allow for more sensitive measurements due to the compensation of experimental errors, temperature fluctuations and other instrument related fluctuations. The time frame between different injections of PSA varies between 35 and 40 min as indicated in FIG. 19.

The camel antibody fragments applied in this study have a molecular weight of 15,000 Daltons while the conventional mouse antibodies have typically a molecular weight of 150,000 Daltons. The camel antibody fragments are therefore almost 10 times smaller than conventional antibodies. The camel antibody fragments applied in this study have only one recognition side/region while conventional mouse antibodies have two recognition binding sites. It is therefore expected that the use of camel antibody fragments enables an increase in the amount of binding sites on the surface of a factor 5 (10/2). However, if one compares the PSA recognition signals for both camel antibody fragments and normal antibodies, the signal on camel antibody fragments exceeds the factor of 5.

This indicates that other factors play a major role. Due to the smaller size of the camel antibody fragments, the recognition event or the PSA binding event happens closer to the surface due to the smaller size of camel antibody fragments compared to conventional mouse antibody fragments. The additional enhancement effect is therefore contributed to by the increased sensitivity of localized surface plasmon resonance upon the use of smaller receptor fragments, which is a advantageous characteristic of this invention. This can be explained by the fact that the sensitivity of this technique decays away from the surface. Applying smaller binding fragments allows monitoring of the binding event at a position were the sensitivity is higher.

Experiment

Figure 20:
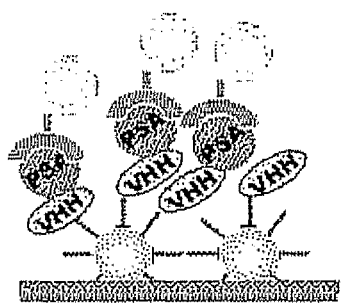
FIG. 20: A schematic illustration of a TPB sandwich approach. From bottom to top: quartz substrate, mercaptosilane adhesion layer, Au 50 nm gold nanoparticles, mixed self-assembled monolayer, camel antibody fragment (VHH), PSA, secondary anti-PSA antibody functionalized with 20 nm gold nanoparticles

Another approach to further increase the sensitivity of the transmission plasmon biosensor technique or the localized surface plasmon biosensor technique is the use of a sandwich assay using colloidal gold functionalized secondary antibodies. An illustration of this approach is shown in FIG. 20

Figure 21:
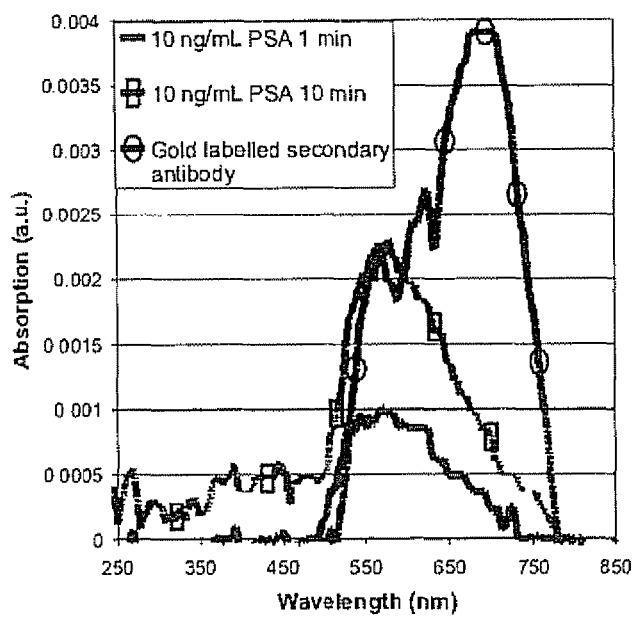
FIG. 21: The detection of 10 ng/mL of PSA via a direct measurement or via an sandwich approach using gold labeled secondary antibodies.

To illustrate the ability of this approach, an anti-PSA antibody should be coupled to the gold nanoparticles. In this specific assay, the anti-PSA antibodies were coupled to commercial 20 nm (supplied by BBI) gold nanoparticles. The anti-PSA antibodies were first biotinylated according to the manufacturers' instructions. Next, 1 mL of BBI nanoparticles were mixed with 250 µg of biotinylated anti-PSA monoclonal mouse antibodies. After mixing and centrifugation, the anti-PSA coated gold nanoparticles were isolated and applied in the localized surface plasmon resonance or Transmission Plasmon Biosensor technique. After functionalization the quartz slides with nanoparticles and camel antibody fragments, 10 ng/mL of PSA in HBS was pursed over the camel antibody fragment coated gold nanoparticle slide. The signal was measured and an additional enhancement effect was observed, which exemplifies the possible sensitivity increases that can be expected using this approach (see FIG. 21).

In the above-mentioned examples the increase is doubled, but additional peaks were observed due to plasmon coupling, which could further increase the sensitivity of this approach.

Experiment

Figure 23:
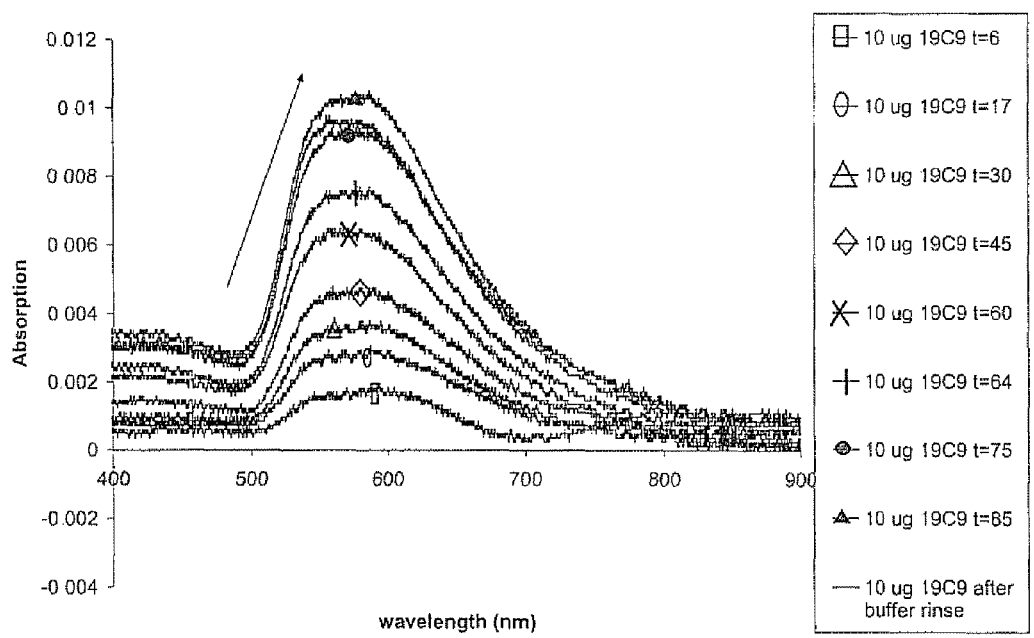
FIG. 23: Changes of the absorption spectra during binding of the anti-penicillin antibodies (clone 19C9) to the ampicillin modified nanoparticle film in function of the time.
Figure 24:
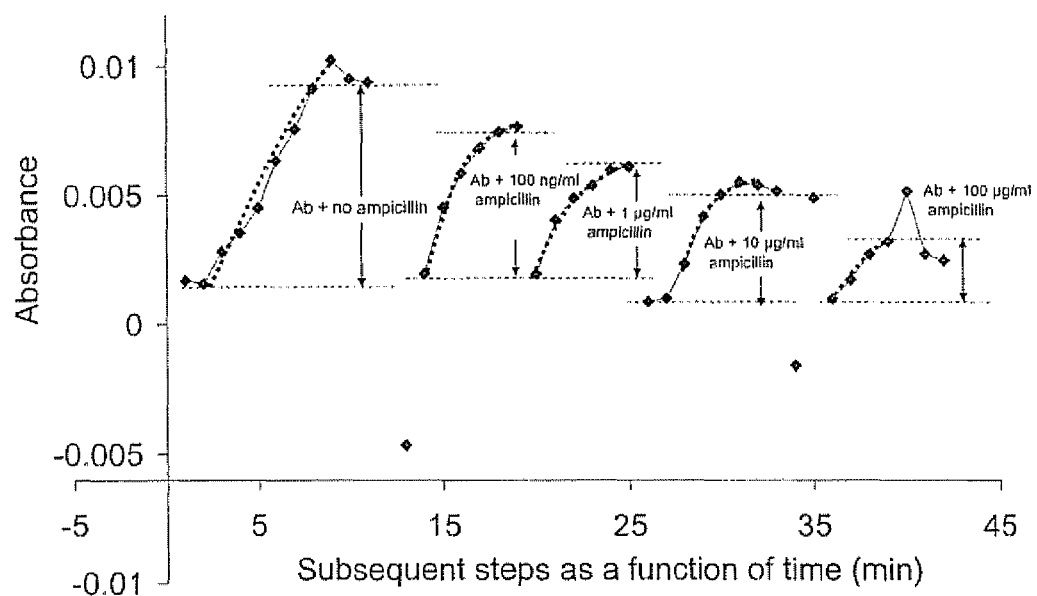
FIG. 24: Changes of the maximum absorption during binding of the anti-penicillin antibodies (clone 19C9) to the ampicillin modified nanoparticle film in function of the time and this in the presence of different concentrations of ampicillin (100 ng/ml-100 µg/ml).

The above-described replacement inhibition assay experiment was performed with ampicillin as an analyte/antigen and 19C9 as penicillin specific monoclonal antibody (mAb). First, anti-ampicillin antibodies were bound onto a nanoparticle film which was functionalized with ampicillin molecules via a self-assembled monolayer (FIGS. 22 and 23). Next, this surface was subjected to the sample containing the analyte (ampicillin) in a high concentration (1 mM). The bound anti-ampicillin antibodies release themselves from the surface due to the competition with the ampicillin molecules in the sample. If mixtures of ampicillin and a fixed concentration of 19C9 are then sent over the surface, the signal will be reversely related to the concentration of ampicillin. If a high concentration of ampicillin is present in the sample, the signal decreases towards zero (FIG. 24).

A detailed description of the experiment is given below. Quartz slides were first cleaned for 10 min with a piranha solution (1/3 $H_2O_2/H_2SO_4$). Subsequently the samples were rinsed with water and functionalized with 3-mercapto-propyltrimethoxysilane (10% (v/v) in 95/5 (v/v) ethanol/water) for 3 h. Next, the samples were rinsed with ethanol and dried in an oven for 10 min at 108° C.

The gold nanoparticles (50 nm) were produced via the procedure described by Frens (Frens, G. *Nat. Phys. Sci.* 1973, 241, 20). The nanoparticles were bound on the mercapto-silane functionalized quartz slides by an overnight incubation. This enables a covalent binding between the thiol-groups on the functionalized quartz slides and the gold surface of the gold nanoparticles. Afterwards, the slides were rinsed with DI water and dried under a stream of nitrogen gas.

Subsequently, the slides were functionalized with thiol molecules to allow the covalent binding of the receptor molecules (in this example the penicillin ampicillin). Therefore, the slides were immersed in a 5/95 (v/v) solution of 1 mM 2-(2-(2-(2-(2-(2-(11-mercaptoundecyloxy)ethoxy)ethoxy) ethoxy)ethoxy)-ethoxy)ethoxyacetic acid and 2-(2-(2-(11-mercaptoundecyloxy)ethoxy)ethoxy)ethanol in ethanol for 1 hours. The resulting surface consisted of a gold nanoparticle surface functionalized with both carboxylic groups to allow the coupling with the receptor molecules and poly(ethylene-oxide) groups to avoid non-specific adsorption.

Via their amino groups, the ampicillin molecules (supplied by Sigma, CAS number 69-52-3) were coupled onto the thiol molecules using a previously described EDC/NHS method (F. Frederix, K. Bonroy, W. Laureyn, G. Reekmans, A. Campitelli, W. Dehaen and G. Maes, 'Enhanced performance of a biological recognition layer based on mixed self-assembled monolayers of thiols on gold', *Langmuir* 2003, 19(10), 4351).

The actual localized surface plasmon resonance or transmission plasmon biosensor experiments were performed using differential measurements with a Shimadzu UV-1601PC spectrophotometer with a slit width of 2 nm and a data interval of 0.5 nm. The aim is to measure binding of penicillin-specific antibodies (monoclonal antibody clone 19C9 (Cliquest P. et al. (2001, J. of Food and Agricultural Chemistry, 49, 3349) in phosphate buffer saline (PBS) (10 mM phosphate, 3 mM KCl, 137 mM NaCl, pH 7.4). The 19C9 binding can be inhibited by ampicillin molecules present in the sample. The inhibition of the 19C9 binding is related to the concentration of ampicillin in the sample. Differential measurements implies that the difference UV-Vis absorption spectrum is measured between an ampicillin coated functionalized quartz slide and slide without ampicillin upon contact with the 19C9 antibody containing sample. Differential measurements allow for more sensitive measurements due to the compensation of experimental errors, temperature fluctuations, and other instrument related fluctuations.

The ampicillin molecules (referred to as an analyte analogue) applied in this study have a molecular weight of ~370 Dalton with a size of less than 2 nm. Due to the smaller size of the analyte analogue compared to bigger receptor molecules, the recognition event or the 19C9 binding event happens closer to the surface. The additional enhancement effect is therefore contributed to by the increased sensitivity of localized surface plasmon resonance upon the use of smaller receptor fragments, which is an advantageous characteristic of this invention. This can be explained by the fact that the sensitivity of this technique decays away from the surface.

CONCLUSION

While a number of aspects and embodiments have been discussed above, it will be appreciated that various modifications, permutations, additions and/or sub-combinations of these aspects and embodiments are possible. It is therefore intended that the following appended claims and claims hereafter introduced are interpreted to include all such modifications, permutations, additions and/or sub-combinations as are within their true spirit and scope.

What is claimed is:

1. A method for determining the concentration of an analyte within a sample, the method comprising:

providing a first substrate comprising a conductive region and a recognition layer, the conductive region having a first surface operatively coupled with the recognition layer, the recognition layer comprising at least one recognition molecule, wherein said conductive region comprises at least one particle formed of a conductive material and having a hollow tubular shape with an average diameter of less than 300 nm and wherein the distance between the first surface of the conductive region and the recognition molecule is selected such that when the analyte is bound to the recognition layer the combination of the at least one particle and the analyte exhibits a particle plasmon effect when radiation is directed through the conductive region and the recognition layer;

contacting the substrate with the sample to bind at least some of any analyte present in the sample with the recognition molecule;

directing radiation through the conductive region and the recognition layer, measuring at least a part of a spectrum of radiation that is absorbed or transmitted by or through the substrate and manifesting a particle plasmon effect;

comparing the at least part of the spectrum with a reference spectrum and determining the difference; and determining the concentration of the analyte from the difference.

2. The method according to claim 1, wherein the distance between said first surface and the part of said recognition molecule where binding takes place is less than 60 nm.

3. The method as recited in claim 1 wherein the distance between said first surface and the part of said recognition molecule where binding takes place is less than 17 nm.

4. The method as recited in claim 1 wherein the distance between said first surface and the part of said recognition molecule where binding takes place is between 4 and 17 nm.

5. The method as recited in claim 1 wherein the recognition molecule is subjected to enzymatic cleavage such that only the active part of the recognition molecules is part of the recognition layer.

6. The method as recited in claim 1 wherein the recognition molecule is a small molecule that functions as a recognition element in an inhibition or replacement assay.

7. The method as recited in claim 1, wherein the at least one particle exhibits a particle plasmon effect and a bulk interband absorption and a plasmon coupling band.

8. The method as recited in claim 1, wherein the at least one particle is formed of metal.

9. The method as recited in claim 1, wherein the at least one particle is an alloy of at least two metals.

10. The method as recited in claim 1, wherein the conductive region comprises semiconductive particles and metallic particles.

11. The method as recited in claim 1, wherein the conductive region comprises at least two particles and the edge to edge distance of the at least two particles is between 1 nm and 5 µm.

12. The method as recited in claim 1, wherein the conductive region comprises at least two particles and the edge to edge distance of the particles is between 1 nm and 1 µm.

13. The method as recited in claim 1, wherein the average diameter of the at least one particle is smaller in dimension than a principal wavelength of the radiation.

14. The method as recited in claim 1, wherein an interaction between the analyte and the recognition layer results in a change in a dielectric constant of the recognition layer.

15. The method as recited in claim 1, wherein the substrate further comprises a support layer and a second surface of the conductive region, the second surface being operatively coupled with the support layer.

16. The method as recited in claim 15, wherein the support layer is optically transparent to the radiation.

17. The method as recited in claim 15, wherein the support layer is optically semi-transparent to the radiation.

18. The method as recited in claim 1, wherein the recognition layer comprises an intermediate layer and a recognition molecule.

19. The method as recited in claim 1, wherein the recognition layer comprises a self-assembling monolayer.

20. The method as recited in claim 1, wherein the substrate comprises a plurality of conductive regions, the plurality of conductive regions being arranged in an array.

21. The method as recited in claim 20, wherein the substrate is arranged as a microtitre plate.

22. The method as recited in claim 1, wherein an intensity of the radiation absorbed or transmitted by or through the substrate is determined as a function of a wavelength of the radiation.

23. A method for determining the concentration of an analyte within a sample, the method comprising:

providing a first substrate comprising a conductive region and a recognition layer, the conductive region having a first surface operatively coupled with the recognition layer, the recognition layer comprising at least one recognition molecule, wherein said conductive region comprises at least one particle formed of a conductive material and having a hollow tubular shape with an average diameter of less than 300 nm and wherein the distance between the first surface of the conductive region and the recognition molecule is selected such that when the analyte is bound to the recognition layer the combination of the at least one particle and the analyte exhibits a particle plasmon effect;

contacting the substrate with the sample to bind at least some of any analyte present in the sample with the recognition molecule;

directing radiation through the conductive region and the recognition layer, measuring at least a part of a spectrum of radiation that is absorbed or transmitted by or through the substrate and manifesting a particle plasmon effect;

providing a second substrate;

subjecting the second substrate to a reference sample;

directing radiation through the second substrate;

measuring the intensity of the radiation absorbed or transmitted by or through the second substrate; and comparing an intensity of the radiation absorbed or transmitted by or through the second substrate with an intensity of the radiation absorbed or transmitted by or through the first substrate to determine the concentration of the analyte on the first substrate.

24. The method of claim 1, wherein the conductive region comprises at least two particles and a combination of the at least two particles and the analyte further exhibits a plasmon coupling effect.

* * * * *